United States Patent
Bar-Or et al.

(10) Patent No.: US 9,372,167 B2
(45) Date of Patent: Jun. 21, 2016

(54) OXIDATION-REDUCTION POTENTIAL TEST DEVICE INCLUDING A MULTIPLE LAYER GEL

(71) Applicant: Aytu BioScience, Inc., Englewood, CO (US)

(72) Inventors: Raphael Bar-Or, Denver, CO (US);
David Bar-Or, Englewood, CO (US);
Leonard T. Rael, Centennial, CO (US)

(73) Assignee: Aytu BioScience, Inc., Englewood, CO (US)

( * ) Notice: Subject to any disclaimer, the term of this patent is extended or adjusted under 35 U.S.C. 154(b) by 504 days.

(21) Appl. No.: 13/866,503

(22) Filed: Apr. 19, 2013

(65) Prior Publication Data
US 2013/0277232 A1    Oct. 24, 2013

Related U.S. Application Data

(60) Provisional application No. 61/635,537, filed on Apr. 19, 2012.

(51) Int. Cl.
*G01N 27/403* (2006.01)
*G01N 27/30* (2006.01)
*G01N 27/327* (2006.01)

(52) U.S. Cl.
CPC .......... *G01N 27/301* (2013.01); *G01N 27/3272* (2013.01); *G01N 27/403* (2013.01)

(58) Field of Classification Search
CPC ..... G01N 27/28; G01N 27/30; G01N 27/301; G01N 27/3272; G01N 27/403
See application file for complete search history.

(56) References Cited

U.S. PATENT DOCUMENTS

| | | | |
|---|---|---|---|
| 3,956,094 A | 5/1976 | Capuano | |
| 4,053,381 A | 10/1977 | Hamblen et al. | |
| 4,225,410 A | 9/1980 | Pace | |
| 4,299,919 A | 11/1981 | Jellinek | |
| 4,545,382 A | 10/1985 | Higgins et al. | |
| 4,571,292 A | 2/1986 | Liu et al. | |

(Continued)

FOREIGN PATENT DOCUMENTS

| | | |
|---|---|---|
| CN | 1301343 | 6/2001 |
| CN | 1776414 | 5/2006 |

(Continued)

OTHER PUBLICATIONS

Fried et al., "Frailty in older adults: evidence for a phenotype," J. Gerontol A Biol Sci Med Sci., 2001, vol. 56(3), pp. M146-M156 (Abstract), 2 pages.

(Continued)

*Primary Examiner* — Alexander Noguerola
(74) *Attorney, Agent, or Firm* — Sheridan Ross P.C.

(57) ABSTRACT

A multiple layer gel and method for forming a multiple layer gel are provided. The multiple layer gel includes an isolation layer and an electrolyte layer. The isolation layer provides a molecular weight screen, to prevent proteins or other molecules from contacting a reference cell covered by the isolation layer. The electrolyte layer covers the isolation layer, and provides a source of ions that place the reference cell in ionic and/or electrical contact with a fluid sample. The multiple layer gel can be used to maintain a reliable reference voltage from an associated reference cell while an electrical potential or other electrical characteristic of a sample fluid is being determined.

29 Claims, 7 Drawing Sheets

(56) References Cited

U.S. PATENT DOCUMENTS

| | | | |
|---|---|---|---|
| 4,865,717 A | 9/1989 | Setter et al. | |
| 4,963,245 A | 10/1990 | Weetall | |
| 4,980,043 A * | 12/1990 | Tomita | G01N 27/301 204/414 |
| 5,073,011 A | 12/1991 | Ito et al. | |
| 5,165,406 A | 11/1992 | Wong | |
| 5,228,972 A | 7/1993 | Osaka et al. | |
| 5,230,786 A | 7/1993 | Preidel | |
| 5,260,321 A | 11/1993 | Hof et al. | |
| 5,267,569 A | 12/1993 | Lienhard | |
| 5,273,639 A | 12/1993 | Kaneko et al. | |
| 5,290,519 A | 3/1994 | Bar-Or et al. | |
| 5,312,590 A | 5/1994 | Gunasingham | |
| 5,334,305 A | 8/1994 | Okada et al. | |
| 5,384,031 A | 1/1995 | Anderson et al. | |
| 5,393,391 A | 2/1995 | Dietze et al. | |
| 5,395,755 A | 3/1995 | Thorpe et al. | |
| 5,401,376 A | 3/1995 | Foos et al. | |
| 5,509,410 A | 4/1996 | Hill et al. | |
| 5,562,815 A | 10/1996 | Preidel | |
| 5,582,698 A | 12/1996 | Flaherty et al. | |
| 5,645,709 A | 7/1997 | Birch et al. | |
| 5,656,142 A | 8/1997 | Park et al. | |
| 5,672,811 A | 9/1997 | Kato et al. | |
| 5,679,532 A | 10/1997 | Repine | |
| 5,728,281 A | 3/1998 | Holmstrom et al. | |
| 5,782,879 A | 7/1998 | Rosborough et al. | |
| 5,799,350 A | 9/1998 | Ferek-Petric et al. | |
| 5,820,551 A | 10/1998 | Hill et al. | |
| 5,906,921 A | 5/1999 | Ikeda et al. | |
| 6,143,164 A | 11/2000 | Heller et al. | |
| 6,177,260 B1 | 1/2001 | Benzie et al. | |
| 6,212,417 B1 | 4/2001 | Ikeda et al. | |
| 6,236,873 B1 | 5/2001 | Holmstrom | |
| 6,269,261 B1 | 7/2001 | Ootomo | |
| 6,280,588 B1 | 8/2001 | Kato et al. | |
| 6,294,062 B1 | 9/2001 | Buck, Jr. et al. | |
| 6,321,101 B1 | 11/2001 | Holmstrom | |
| 6,340,428 B1 | 1/2002 | Ikeda et al. | |
| 6,369,106 B1 | 4/2002 | Atlas et al. | |
| 6,429,021 B1 | 8/2002 | Qian et al. | |
| 6,447,670 B1 | 9/2002 | Holmstrom | |
| 6,599,746 B1 | 7/2003 | Gumbrecht | |
| 6,607,658 B1 | 8/2003 | Heller et al. | |
| 6,720,107 B1 * | 4/2004 | Holtom | B60L 3/0046 429/105 |
| 6,749,740 B2 | 6/2004 | Liamos et al. | |
| 6,790,327 B2 | 9/2004 | Ikeda et al. | |
| 6,793,632 B2 | 9/2004 | Sohrab | |
| 7,063,782 B2 | 6/2006 | Wayment et al. | |
| 7,125,723 B2 | 10/2006 | Popov et al. | |
| 7,132,296 B2 | 11/2006 | Ou et al. | |
| 7,134,602 B2 | 11/2006 | Harima | |
| 7,267,750 B2 | 9/2007 | Watanabe et al. | |
| 7,459,066 B2 | 12/2008 | Broadley et al. | |
| 7,618,522 B2 | 11/2009 | Davies | |
| 7,949,473 B2 | 5/2011 | Rauh | |
| 8,317,997 B2 | 11/2012 | Bar-Or et al. | |
| 8,329,012 B2 | 12/2012 | Bar-Or et al. | |
| 2002/0115619 A1 | 8/2002 | Rubenstein et al. | |
| 2004/0171112 A1 | 9/2004 | Remington et al. | |
| 2005/0074893 A1 | 4/2005 | Horiguchi et al. | |
| 2005/0142613 A1 | 6/2005 | Bar-Or et al. | |
| 2005/0182568 A1 | 8/2005 | Duraffourd et al. | |
| 2005/0244983 A1 | 11/2005 | Ching | |
| 2006/0006122 A1 | 1/2006 | Burns et al. | |
| 2006/0258973 A1 | 11/2006 | Volt | |
| 2007/0020181 A1 | 1/2007 | Workman et al. | |
| 2007/0111104 A1 * | 5/2007 | Shibuya | H01M 4/139 429/303 |
| 2008/0052130 A1 | 2/2008 | Iliff | |
| 2008/0269167 A1 | 10/2008 | Ziegler et al. | |
| 2009/0000947 A1 | 1/2009 | Akahori et al. | |
| 2009/0004686 A1 | 1/2009 | Bar-Or et al. | |
| 2010/0267074 A1 | 10/2010 | Bar-Or et al. | |
| 2010/0270149 A1 | 10/2010 | Wang et al. | |
| 2011/0056831 A1 | 3/2011 | Kendig et al. | |
| 2012/0325685 A1 | 12/2012 | Bar-Or et al. | |
| 2013/0043142 A1 | 2/2013 | Bar-Or et al. | |
| 2014/0004551 A1 | 1/2014 | Bar-Or et al. | |

FOREIGN PATENT DOCUMENTS

| | | |
|---|---|---|
| CN | 1875265 | 12/2006 |
| DE | 202005009988 | 10/2005 |
| EP | 0634488 | 1/1995 |
| JP | 60-62978 | 4/1985 |
| JP | H08-94574 | 4/1996 |
| JP | H08-509617 | 10/1996 |
| JP | H09-178690 | 7/1997 |
| JP | H09-304330 | 11/1997 |
| JP | H09-327443 | 12/1997 |
| JP | H10-232219 | 9/1998 |
| JP | H11-83797 | 3/1999 |
| JP | 2000-002683 | 1/2000 |
| JP | 2000-088801 | 3/2000 |
| JP | 2001-021527 | 1/2001 |
| JP | 2001-289812 | 10/2001 |
| JP | 2002-207037 | 7/2002 |
| JP | 2002-535615 | 10/2002 |
| JP | 2003-503702 | 1/2003 |
| JP | 2003-202317 | 7/2003 |
| JP | 2004-117084 | 4/2004 |
| JP | 2006-508349 | 3/2006 |
| JP | 2007-057459 | 3/2007 |
| JP | 3971097 | 9/2007 |
| JP | 2009-075127 | 4/2009 |
| JP | 2010-96724 | 4/2010 |
| JP | 2012-047647 | 3/2012 |
| RU | 2241997 | 12/2004 |
| WO | WO 94/25626 | 11/1994 |
| WO | WO 01/25776 | 4/2001 |
| WO | WO 03/071266 | 8/2003 |
| WO | WO 2004/068140 | 8/2004 |
| WO | WO 2007/039775 | 4/2007 |
| WO | WO 2007/059455 | 5/2007 |

OTHER PUBLICATIONS

Siesjö et al., "Free radicals and brain damage," Cerebrovasc Brain Metab Rev, 1989, vol. 1(3), pp. 165-211 (Abstract), 1 page.

U.S. Appl. No. 14/061,482, filed Nov. 8, 2013, Bar-Or et al.

Abiles et al., "Oxidative stress is increased in critically ill patients according to antioxidant vitamins intake, independent of severity: a cohort study," Oct. 13, 2006, available online at www.ccforum.com/content/10/5/R146, 9 pages.

Chevion et al., "Evaluation of Plasma Low Molecular Weight Antioxidant Capacity by Cyclic Voltammetry," Free Radical Biol. Med., 1997, vol. 22(3), pp. 411-421.

Chevion et al., "The Use of Cyclic Voltammetry for the Evaluation of Antioxidant Capacity," Free Radical Biol. Med., 2000, vol. 28(6), pp. 860-870.

Ernst et al., "Electrochemical characterisation of uric acid and ascorbic acid at a platinum electrode," Analytica Chimica ACTA, 2001, vol. 449, pp. 129-134.

Kinumi, "Protein Modification due to Oxidative Stress," Sansouken Today, May 2006, vol. 6(5), pp. 28-29 (no English translation available).

Prasad et al., "Evaluation of oxidative stress after fractures. A preliminary study," Acta Orthopaedica Belgica, 2003, vol. 69(6), pp. 546-551.

U.S. Appl. No. 14/061,482, filed Oct. 23, 2013, Bar-Or et al.
U.S. Appl. No. 14/144,154, filed Dec. 30, 2013, Bar-Or et al.
U.S. Appl. No. 14/222,075, filed Mar. 21, 2014, Bar-Or et al.

Reuter et al., "Oxidative stress, inflammation, and cancer: How are they linked?" Free Radical Biol. Med., 2010, vol. 49(11), pp. 1603-1616 [doi:10.1016/j.freeradbiomed.2019.09.06], 40 pages.

Turk et al., "Promotion of Fracture Healing by Vitamin E in Rats," Journal of International Medical Research, 2004, vol. 32(5), pp. 507-512.

(56) References Cited

OTHER PUBLICATIONS

Yeler et al., "Investigation of oxidative stress during fracture healing in the rats," Cell Biochemistry and Function, 2005, vol. 23(2), pp. 137-139.
Written Opinion for International (PCT) Patent Application No. PCT/US08/63855, mailed Aug. 26, 2008, 8 pages.
International Search Report for International (PCT) Patent Application No. PCT/US08/63855, mailed Aug. 26, 2008, 3 pages.
International Preliminary Report on Patentability for International (PCT) Patent Application No. PCT/US08/63855, mailed Nov. 24, 2009, 10 pages.
Extended European Search Report for European Patent Application No. 08755661.9, dated Aug. 3, 2010, 7 pages.
International Search Report for International (PCT) Patent Application No. PCT/US2012/026884, mailed Jun. 21, 2012 4 pages.
Written Opinion for International (PCT) Patent Application No. PCT/US2012/026884, mailed Jun. 21, 2012 6 pages.
International Preliminary Report on Patentability for International (PCT) Patent Application No. PCT/US2012/026884, mailed Sep. 3, 2013 8 pages.
Official Action for Australia Patent Application No. 2013249126, dated Mar. 2, 2015 3 pages.
Official Action for New Zealand Patent Application No. 700923, dated Feb. 10, 2015 3 pages.
International Preliminary Report on Patentability for International Patent Application No. PCT/US13/37357, mailed Oct. 30, 2014, 9 pages.
International Search Report and Written Opinion for International Patent Application No. PCT/US13/66432, mailed May 13, 2014, 16 pages.
Alonso De Vega et al., "Oxidative Stress in Critically Ill Patients with Systemic Inflammatory Response Syndrome," Critical Care Medicine, vol. 30, No. 8 (Aug. 2002), pp. 1782-1786, (Abstract).
Alonso De Vega et al., "Plasma Redox Status Relates to Severity in Critically Ill Patients," Critical Care Medicine, vol. 28, No. 6 (Jun. 2000), pp. 1812-1814, (Abstract).
Ascensão et al., "Biochemical Impact of a Soccer Match—Analysis of Oxidative Stress and Muscle Damage Markers Throughout Recovery," Clinical Biochemistry, vol. 41, No. 10-11 (Jul. 2008), pp. 841-851, (Abstract).
Author Unknown, "Glucose meter," available at http://en.wikipedia.org/wiki/Glucose_meter, printed on Jun. 14, 2009, 7 pages.
Author Unknown, "Materials for Diagnostic Assays," PALL Life Sciences, Mar. 2009, 8 pages.
Author Unknown, "Orion pH, ORP and ISE Theory," Thermo Electron Corporation, Mar. 24, 2004, 9 pages.
Author Unknown, "Oxidation Reduction Potential (ORP): A New Tool for Evaluating Water Sanitation", Hybrid, Hendrix Genetics Company, Dec. 17, 2010, 4 pages.
Author Unknown, "Redox electrode," Unisense Science, as late as Jun. 6, 2009, 2 pages.
Author Unknown, "Universal Reduction-Oxidation (REDOX) electrode for the Temporal Measurement of the Redox Potential Health and Disease," VCU Technology Transfer Marketing Flyer, as early as Apr. 12, 2007, 1 page, available at http://www.research.vcu.edu/ott/licensable_technologies/flash/05-70_ward.htm.
Baig et al., "Comparison between Bed Side Testing of Blood Glucose by Glucometer vs Centralized Testing in a Tertiary Care Hospital," J. Ayub Med Coli Abbottabad vol. 19(3), 2007, 5 pages.
Bar-Or et al., "Heterogeneity and Oxidation Status of Commerical Human Albumin Preparations in Clinical Use," Critical Care Medicine, Jul. 2005, vol. 33, No. 7, pp. 1638-1641.
Bayir et al., "Assessment of Antioxidant Reserves and Oxidative Stress in Cerbrospinal Fluid after Severe Traumatic Brain Injury in Infants and Children," Pediatric Research, 2002, vol. 51(5), pp. 571-578.
Biffl et al., "Plasma from Aged Stored Red Blood Cells Delays Neutrophil Apoptosis and Primes for Cytotoxicity: Abrogation by Poststorage Washing but not Prestorage Leukoreduction," The Journal of Trauma, vol. 50, No. 3 (Mar. 2001), pp. 426-432, (Abstract).

Brittingham et al., "Febrile Transfusion Reactions Caused by Sensitivity to Donor Leukocytes and Platelets," Journal of the American Medical Association, vol. 165, No. 7 (Oct. 19, 1957), pp. 819-825, (Abstract).
Carballal et al., "Sulfenic Acid Formation in Human Serum Albumin by Hydrogen Peroxide and Peroxynitrite," Biochemistry, vol. 42 (2003), pp. 9906-9914.
Cases et al., "Response of antioxidant defences to oxidative stress induced by prolonged exercise: antioxidant enzyme gene expression in lymphocytes," European Journal of Applied Physiology, vol. 98, No. 3 (Oct. 2006), pp. 263-269.
Cernak et al. "Characterization of Plasma Magnesium Concentration and Oxidative Stress Following Graded Traumatic Brain Injury in Humans," Journal of Neurotrauma, Jan. 2000, vol. 17, No. 1, pp. 53-68.
Codd et al., "Redox Maintenance and Organ Preservation," Transplantation Proceedings, vol. 9, No. 3 (Sep. 1977), pp. 1569-1571, (Abstract).
Codd et al., "Redox Maintenance in Restoration of Organ Viability," The Journal of Surgical Research, vol. 22, No. 5 (May 1977), pp. 585-592, (Abstract).
Collins et al., "Optimal Redox Electrode Potential for 24-Hour Rabbit Kidney Perfusion," The Journal of Surgical Research, vol. 39, No. 3 (Sep. 1985), pp. 246-250, (Abstract).
Cowley et al., Plasma antioxidant potential in severe sepsis: A comparison of survivors and nonsurvivors, Critical Care Medicine, vol. 24, No. 7 (Jul. 1996), pp. 1179-1183, available at http://www.ccmjournal.com/pt/re/ccm/fulltext.oooo3246-199607000-00019htm;jsessionid=F2GT . . . .
Dosek et al., "High Altitude and Oxidative Stress," Respiratory Physiology & Neurobiology, vol. 158, No. 2-3 (Sep. 30, 2007), pp. 128-131, (Abstract).
EcoScan 5 & 6 Series, Economy Handheld, Eutech Instruments, May 16, 2007, 12 pages.
Elokda et al., "Effects of Exercise Training on the Gluthathione Antioxidant System," European journal of Cardiovascular Prevention and Rehabilitation : Official Journal of the European Society of Cardiology, Working Groups on Epidemiology & Prevention and Cardiac Rehabilitation and Exercise Physiology, vol. 14, No. 5 (Oct. 2007), pp. 630-637, (Abstract).
Ferretti et al., "Copper-induced Oxidative Damage on Astrocytes: Protective Effect Exerted by Human High Density Lipoproteins," Biochimica et biophysica acta, vol. 1635, No. 1 (Nov. 30, 2003), pp. 48-54.
Ferretti et al., "Paraoxonase Activity in High-Density Lipoproteins: A Comparison between Health and Obese Females," The Journal of Clinical Endocrinology & Metabolism, vol. 90, No. 3 (Mar. 2005), pp. 1728-1733.
Ferretti et al., "Protective Effect of Paroxonase Activity in High-density Lipoproteins Against Erythrocyte Membranes Peroxidation: A Comparison Between Healthy Subjects and Type 1 Diabetic Patients," The Journal of Clinical Endocrinology and Metabolism, vol. 89, No. 6 (Jun. 2004), pp. 2957-2962.
Galley et al., "Xanthine Oxidase Activity and Free Radical Generaton in Patients with Sepsis," Critical Care Medicine, vol. 24, No. 10 (Oct. 1996), pp. 1649-1653, (Abstract).
Ghiselli et al., "Total Antioxidant Capacity as a Tool to Assess Redox Status: Critical View and Experimental Data," Free Radical Biology & Medicine, vol. 29, No. 11 (Dec. 2000), pp. 1106-1114, (Abstract).
Gomez-Cabrera et al., "Moderate Exercise in an Antioxidant: Upregulation of Antioxidant genes by Training," Free Radical Biology & Medicine, vol. 44, No. 2 (Jan. 15, 2008), pp. 126-131, (Abstract).
Goode et al., "Decreased Antioxidant Status and Increased Lipid Perosidation in Patients with Septic Shock and Secondary Organ Dysfunction," Critical Care Medicine, vol. 23, No. 4 (Apr. 1995), pp. 646-651, (Abstract).
Green et al., "Effluent Redox Potential: A Rapid Method for Assaying Warm Ischemic Injury," The Journal of Surgical Research, vol. 25, No. 3 (Sep. 1978), pp. 222-225, (Abstract).
Gubler et al. "Trauma Recidivism in the Elderly," The Journal of Trauma: Injury, Infection, and Critical Care, Dec. 1996, vol. 41, No. 6, pp. 952-956.

(56) References Cited

OTHER PUBLICATIONS

Horton, "Free Radicals and Lipid Peroxidation Mediated Injury in burn Trauma: The Role of Antioxidant Therapy," Toxicology, vol. 189, No. 1-2 (Jul. 15, 2003), pp. 75-88, (Abstract).
Huang et al., "The Chemistry behind Antioxidant Capacity Assays," Journal of Agriculture and Food Chemistry, vol. 53 (2005), pp. 1841-1856.
Jellinek et al., "Electrochemical Control of Redox Potential in Perfusate for Prolonged Heart Storage," Transactions—American Society for Artificial Internal Organs, vol. 20 (1974), pp. B:533-537, (Abstract).
Jellinek et al., "Oxidation-Reduction Maintenance in Organ Preservation," Archives of Surgery, vol. 120, No. 4 (Apr. 1985), pp. 439-442, (Abstract).
Ji, "Antioxidants and Oxidative Stress in Exercise," Proceedings of the Society for Experimental Biology and Medicine, Society for Experimental Biology and Medicine (New York, N.Y.), vol. 222, No. 3 (Dec. 1999), pp. 283-292.
Ji, "Modulation of Skeletal Muscle Antioxidant Defense by Exercise: Role of Redox Signaling," Free Radical Biology & Medicine, vol. 44, No. 2 (Jan. 15, 2008), pp. 142-152 (Abstract).
Kohen et al., "Noninvasive in vivo evaluation of skin antioxidant activity and oxidation status," Methods in Enzymology, vol. 300 (1999), pp. 428-437.
Kohen et al., "Quantification of the overall reactive oxygen species scavenging capacity of biological fluids and tissues," Free Radical Biology & Medicine, vol. 28, No. 6 (Mar. 15, 2000), pp. 871-879.
Kyparos et al., "Short Duration Exhaustive Aerobic Exercise Induces Oxidative Stress: A Novel Play-oriented Volitional Fatigue Test," The Journal of Sports Medicine and Physical Fitness, vol. 47, No. 4 (Dec. 2007), pp. 483-490, (Abstract).
Lamprecht et al., "Single Bouts of Exercise Affect Albumin Redox State and Carbonyl Groups on Plasma Protein of Trained Men in a Workload Dependent Manner," Journal of Applied Physiology, vol. 104, No. 6 (Jun. 2008), pp. 1611-1617, (Abstract).
Lee et al., "A cobalt-coated needle-type microelectrode array sensor for in situ monitoring of phosphate," J. Micromech. Microeng., vol. 19, 2009, 2 pages, Abstract.
Lee et al., "Fabrication of microelectrode arrays for in situ sensing of oxidation reduction potentials," Sensors & Actuators B: Chem., vol. 115(1), May 23, 2006, 3 pages, Abstract.
Lekhi et al., "Influence of Exercise on Oxidant Stree Products in Elite Indian Cyclists," British Journal of Sports Medicine, vol. 41, No. 10 (Oct. 2007), pp. 691-693, (Abstract).
Lemineur et al., "Biomarkers of oxidative stress in critically ill patients: What should be measured, when and how?" Curr. Opin. Clin. Nutr. Metabol. Care, Nov. 2006, vol. 9(6), pp. 704-710.
Margonis et al., "Oxidative Stress Biomarkers Responses to Physical Overtraining: Implications for Diagnosis," Free Radical Biology and Medicine, vol. 43, No. 6 (Sep. 15, 2007), pp. 901-910, (Abstract).
Mayer et al., "Reduced serum total reductive capacity in lethal severe trauma," The Journal of Trauma, vol. 51, No. 1 (Jul. 2001), pp. 88-91.
McAnulty et al., "Influence of Carbohydrate, Intense Exercise, and Rest Intervals on Homonal and Oxidative Changes," International Journal of Sport Nutrition and Exercise Metabolism, vol. 17, No. 5 (Oct. 2007), pp. 478-490, (Abstract).
Meijer, "Exercise-induced oxidative stress in older adults as measure by antipyrine oxidation," Metabolism, vol. 50, No. 12 (Dec. 2001), pp. 1484-1488, (Abstract).
Michailidis et al., "Sampling Time is Critical for Measurement of Aerobic exercise-induced oxidative Stress," Medicine and Science in Sports and Exercise, vol. 39, No. 7 (Jul. 2007), pp. 1107-1113, (Abstract).
Miller et al., "Acute Respiratory Distress Syndrome in Blunt Trauma: Identification of Independent Risk Factors," The American Surgeon, vol. 68, No. 10 (Oct. 2002), pp. 845-851, (Abstract).
Miller et al., "Improved Myocardial Preservation by Control of the Oxidation-Reduction Potential," The Journal of Heart Transplantation, vol. 4, No. 3 (May 1985), pp. 319-324, (Abstract).

Nikolaidis et al., "Decreased Blood Oxidative Stress After Repeated Muscle-Damaging Exercise," Medicine and Science in Sports and Exercise, vol. 39, No. 7 (Jul. 2007), pp. 1080-1089, (Abstract).
Paschalis et al., "Uniform and Prolonged Changes in Blood Oxidative Stress After Muscle-damaging Exercise," In vivo (Athens, Greece), vol. 21, No. 5 (Sep.-Oct. 2007), pp. 877-883, (Abstract).
Popov et al., "Photochemiluminescent detection of antiradical activity. VI. Antioxidant characeristics of human blook plasma, low density lipoprotein, serum albumin and amino acids during in vitro oxidation," Luminescence, vol. 14, 1999, pp. 169-174.
Popov et al., "Photochemiluminescent detection of antiradical activity. VII. Comparison with a modified method of thermo-initiated free radical generation with chemiluminescent detection," Luminescence, vol. 20, 2005, pp. 321-325.
Prior et al., "In Vivo Total Antioxident Capacity: Comparison of Different Analytical Methods," Free Radical Biology & Medicine, vol. 27, Nos. 11-12 (1999), pp. 1173-1181.
Prokhorov et al., "A method of redoxometry in clinical studies,"Vopr. Med. Khim., vol. 35, No. 5 (Sep.-Oct. 1989), pp. 2-6, (Abstract).
Radak et al., "Effects of Exercise on Brain Function: Role of Free Radicals," Applied Physiology, Nutrition, and Metabolism, vol. 32, No. 5 (Oct. 2007), pp. 942-946, (Abstract).
Radak et al., "Exercise, Oxidative Stress and Hormesis," Ageing Research Reviews, vol. 7, No. 1 (Jan. 2008), pp. 34-42, (Abstract).
Radak et al., "Systemic Adaptation to Oxidative Challenge Induced by Regular Exercise," Free radical Biology & Medicine, vol. 44, No. 2 (Jan. 15, 2008), pp. 153-159, (Abstract).
Rael et al., "Combined cupric-and cuprous-binding peptides are effective in preventing IL-8 release from endothelial cells and redox reactions," Biochemical and Biophysical Research Communications, vol. 357 (2007), pp. 543-548.
Rael et al., "Oxidation-reduction potential and paraxonase-arylesterase activity in trauma patients," Biochemical and Biophysical Research Communications, vol. 361 (2007), pp. 561-565.
Rael et al., "Plasma oxidation-reduction potential and protein oxidation in traumatic brain injury," J. Neurotrauma, Aug. 2009, vol. 26(8), pp. 1203-1211.
Rael et al., "The effect of storage on the accumulation of oxidative biomarkers in donated packed red blood cells," J. Trauma, Jan. 2009, vol. 66(1), pp. 76-81.
Rahnama et al., "Oxidative Stress responses in Physical Education Students During 8 Weeks Aerobic Training," The Journal of Sports Medicine and Physical Fitness, vol. 47, No. 1 (Mar. 2007), pp. 119-123, (Abstract).
Rana et al., "Study on Oxidative Stress in Patients with Abdominal Trauma," Molecular and Cellular Biochemistry, vol. 291, No. 1-2 (Oct. 2006), pp. 161-166, (Abstract).
Rao et al., "Redox Potential Measurements of Plasma in Patients Undergoing Coronary Artery Bypass Graft and Its Clinical Significance," Journal of Pharmacological and Toxicological Methods, vol. 38 (1997), pp. 151-156.
Rice-Evans, "Measurement of Total Antioxidant Activity as a Marker of Antioxidant Status in Vivo: Procedures and Limitations," Free Radical Research, vol. 33, Supplement (Nov. 2000), pp. 59-66, (Abstract).
Rosenberg et al. "Who bounces back? Physiologic and other predictors of intensive care unit readmission," Critical Care Medicine, Mar. 2001, vol. 29, No. 3, pp. 511-518.
Sauaia et al., "Early Predictors of Postinjury Multiple Organ Failure," Archives of Surgery, vol. 129, No. 1 (Jan. 1994), pp. 39-45, (Abstract).
Sen et al., "Antioxidants in Exercise Nutrition," Sports Medicine (Auckland, N.Z.), vol. 31, No. 13 (2001), pp. 891-898, (Abstract).
Shin et al., "Exercise Training Improves the Antioxidant Enzyme Activity with no Change of Telomere Length," Mechanisms of Ageing and Development, vol. 129, No. 5 (May 2008), pp. 254-260, (Abstract).
Shing et al., "The Effect of Consecutive Days of Exercise on Markers of Oxidative Stress," Applied Physiology, Nutrition, and Metabolism, vol. 32, No. 4 (Aug. 2007), pp. 677-685, (Abstract).
Soffler, "Oxidative Stress," The Veterinary Clinics of North America. Equine Practice, vol. 23, No. 1 (May 2007), pp. 135-157 (Abstract).

(56) References Cited

OTHER PUBLICATIONS

Steinberg et al., "Cytokine and Oxidative responses to Maximal Cycling Exercise in Sedentary Subjects," Medicine and Science in Sports and Exercise, vol. 39, No. 6 (Jun. 2007), pp. 964-968, (Abstract).
Vollard et al., "Exercise-induced oxidative stress: Myths, realities and physiological relevance," Sports Med., 2005, vol. 35(12), pp. 1045-1062.
Williams et al., "Dietary Supplements and Sports Performance: Introduction and Vitamins," Journal of the International Society of Sports Nutrition, vol. 1, No. 2 (2004), pp. 1-6.
Winterbourn et al., "Protein Carbonyl Measurements Show Evidence of Early Oxidative Stress in Critically Ill Pateints," Critical Care Medicine, vol. 28, No. 1 (Jan. 2000), pp. 275-277 (Abstract).
Yu et al., "Stratification and Oxidation-Reduction Potential Change in an Aerobic and Sulfate-Reducing Biofilm Studied Using Microelectrodes," JSTOR: Water Environment Research, vol. 73, No. 3, May-Jun. 2001, 2 pages, Abstract.
Zoppi et al., "Overreaching-induced oxidative stress, enhanced HSP72 expression, antioxidant and oxidative enymes downregulaltion," Scandinavian Journal of Medicine & Science in Sports, vol. 18, No. 1 (Feb. 2008), pp. 67-76 (Abstract).
International Search Report and Written Opinion for International Patent Application No. PCT/US13/37357, mailed Aug. 26, 2013, 10 pages.
Ridley "The recognition and early management of critical illness," Annals of the Royal College of Surgeons of England, Sep. 2005, vol. 87, No. 5, pp. 315-322.
Roth et al., "Assessing the antioxidative status in critically ill patients," Current Opinion in Clinical Nutrition and Metabolic Care, vol. 7 (2004), pp. 161-168.
Senior et al., "Effect of Revascularization on Left Ventricular Remodeling in Patients With Heart Failure from Severe Chronic Ischemic Left Ventricular Dysfunction," Am. J. Cardiology, 2001, vol. 88(6), pp. 624-629.
Veglia et al., "Age- and gender-related oxidative status determined in healthy subjects by means of Oxy-Score, a potential new comprehensive index," Biomarkers, vol. 11, No. 6 (Nov.-Dec. 2006), pp. 562-573.
Notice of Acceptance for Australia Patent Application No. 2013249126, dated Sep. 21, 2015 2 pages.
Official Action for Canada Patent Application No. 2,869,151, dated Dec. 8, 2015 3 pages.
Official Action with English Translation for China Patent Application No. 201380026221.X, dated Sep. 6, 2015 17 pages.
Extended Search Report for European Patent Application No. 13778387.4, dated Jan. 13, 2016 8 pages.
Official Action with English Translation for Japan Patent Application No. 2015-507217, dated Nov. 24, 2015.
Official Action for New Zealand Patent Application No. 700923, dated Sep. 4, 2015 2 pages.

* cited by examiner

OXIDATION-REDUCTION POTENTIAL TEST DEVICE INCLUDING A MULTIPLE LAYER GEL

CROSS-REFERENCE TO RELATED APPLICATIONS

This application claims the benefit of U.S. Provisional Patent Application Ser. No. 61/635,537, filed Apr. 19, 2012, the entire contents of which are hereby incorporated herein by reference in their entirety.

FIELD

The present invention relates to multiple layer gels for use with electrochemical reference cells, and methods for depositing multiple layer gels on electrochemical reference cells.

BACKGROUND

Whole blood and blood products, such as plasma and serum, have oxidation-reduction potentials (ORP). Clinically the ORP of blood, plasma and serum provides a diagnostic assay of the oxidative status of an animal. More particularly, researchers have determined that the ORP of blood, plasma and serum is related to health and disease.

An oxidation-reduction system, or redox system, involves the transfer of electrons from a reductant to an oxidant according to the following equation:

$$\text{oxidant} + ne^- \leftrightarrow \text{reductant} \qquad (1)$$

where $ne^-$ equals the number of electrons transferred. At equilibrium, the redox potential (E), or oxidation-reduction potential (ORP), is calculated according to the Nernst-Peters equation:

$$E(ORP) = E_o - RT/nF \ln [\text{reductant}]/[\text{oxidant}] \qquad (2)$$

where R (gas constant), T (temperature in degrees Kelvin) and F (Faraday constant) are constants. $E_o$ is the standard potential of a redox system measured with respect to a hydrogen electrode, which is arbitrarily assigned an $E_o$ of 0 volts, and n is the number of electrons transferred. Therefore, ORP is dependent on the total concentrations of reductants and oxidants, and ORP is an integrated measure of the balance between total oxidants and reductants in a particular system. As such, ORP provides a measure of the overall oxidative status of a body fluid or tissue of a patient.

An ORP measurement which is significantly higher than that of normals will indicate the presence of oxidative stress. The presence of oxidative stress has been related to many diseases, and it has been found to occur in all types of critical illnesses. Accordingly, an ORP level significantly higher than that of healthy individuals indicates the presence of a disease and perhaps a critical illness. An ORP measurement which is the same as or lower than that of healthy individuals indicates the absence of oxidative stress and the absence of a disease or critical illness although an overly low number could indicate a problem as well. Thus, the ORP level of a patient can be used by a medical doctor or veterinarian as an aid in diagnosing or ruling out the presence of a disease, particularly a serious illness. Sequential measurements of ORP over time can be used to monitor the progression of a disease and the effectiveness or lack of effectiveness of treatment of the disease. If a patient's ORP does not decrease after treatment, or especially if it increases despite treatment, this may indicate a poor prognosis and the need for more aggressive and/or additional and/or different treatments. In the case of a measurement made by a patient, such as a patient experiencing symptoms of myocardial infarction, the ORP level may indicate the need for the patient to see a doctor or to immediately proceed to an emergency room for treatment.

Oxidative stress is caused by a higher production of reactive oxygen and reactive nitrogen species or a decrease in endogenous protective antioxidant capacity. Oxidative stress has been related to various diseases and aging, and it has been found to occur in all types of critical illnesses. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. Several investigations have shown a close association between the oxidative status of a critically ill patient and the patient's outcome. See Roth et al., *Current Opinion in Clinical Nutrition and Metabolic Care*, 7:161-168 (2004).

Oxidative stress in patients has been evaluated by measuring various individual markers. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. However, such measurements are often unreliable and provide conflicting and variable measurements of the oxidative status of a patient. See Veglia et al., *Biomarkers*, 11(6): 562-573 (2006); Roth et al., *Current Opinion in Clinical Nutrition and Metabolic Care*, 7:161-168 (2004). The measurement of multiple markers which are then used to provide a score or other assessment of the overall oxidative status of a patient has been developed to overcome the problems of using measurements of single markers. See Veglia et al., *Biomarkers*, 11(6): 562-573 (2006); Roth et al., *Current Opinion in Clinical Nutrition and Metabolic Care*, 7:161-168 (2004). Although such approaches are more reliable and sensitive than measurements of a single marker, they are complex and time consuming. Thus, there is a need for a simpler and faster method for reliably measuring the overall oxidative status of a patient.

The oxidation/reduction potential can be measured electrochemically. Electrochemical devices for measuring ORP of blood and blood products typically require large sample volumes (that is, ten to hundreds of milliliters) and long equilibrium periods. Furthermore, the electrochemical devices have large, bulky electrodes that require cleaning between sample measurements. Such electrochemical devices are poorly suited for routine clinical diagnostic testing. It has been suggested to use electrodes that have undergone treatment to prevent biofouling of the electrode surface. However, such devices necessarily involve complex manufacturing techniques. Moreover, conventional electrochemical devices have not provided a format that is convenient for use in a clinical setting.

The oxidative and radical characteristics of human blood plasma and its blood components (such as low density lipoproteins, serum albumin, and amino acids) can also be determined from photo chemiluminescence, with and without thermo-initiated free radical generation. A photo chemiluminescent system generally includes a free radical generator and a detector that measures chemiluminometric changes in the presence of an antioxidant. More specifically, the blood plasma sample (or one of its components) containing an amount of antioxidant is contacted and reacted with a known amount of free radicals. The free radicals remaining after contacting the blood plasma sample are determined chemiluminometrically. This type of measurement and detection system is not suitable for rapid, large scale measurements of blood plasma samples in a clinical setting.

SUMMARY

Systems are being developed that allow for the ORP of a fluid sample to be measured rapidly and conveniently using a test strip and a readout device. In such systems, the test strip incorporates an electrochemical reference cell or half-cell. In order to obtain an accurate ORP measurement, the materials that are allowed to come into contact with the reference cell should be controlled. Accordingly, embodiments of the present disclosure provide a protective element, in the form of a multiple layer gel, that generally covers at least portions of the reference cell of a test strip.

In accordance with embodiments of the present disclosure, a test strip incorporating a multiple layer gel as disclosed herein is provided as part of systems and methods for measuring oxidation-reduction potential (ORP) that are suitable for rapid, routine clinical diagnostic testing. The complete system generally includes a readout device in addition to the test strip. Embodiments of the present invention system can determine the ORP of a body fluid of a patient, including blood, plasma and serum, or a fluid from an in vitro source, such as, but not limited to extracellular and intracellular fluids (as for example, aqueous humour, vitreous humour, breast milk, cerebrospinal fluid, cerumen, endolymph, perilymph, gastric juice, mucus, peritoneal fluid, pleural fluid, salvia, sebum, semen, sweat, tears, vaginal secretion, vomit, and urine).

The test strip generally includes a substrate, one or more test leads, a reference lead, a reference cell, a multiple layer gel, and a bridge. In a preferred embodiment, the one or more test leads, the reference lead, the reference cell, the multiple layer gel, and the bridge are located between an overlay and the substrate. The test strip can also include a filter. The filter can be provided separately, and/or can form the bridge. A sample chamber generally encompasses at least a portion of the bridge and a portion of each of the one or more test leads. The one or more test leads may comprise a working electrode and a counter electrode. In one embodiment, a sample region comprising the sample chamber is defined by an aperture, the aperture being contained within the overlay. Alternatively or in addition, the sample chamber includes a depression or well within the substrate, or an aperture or well in an intermediate layer. The sample chamber is generally configured to contain a fluid sample, such as blood and/or a blood product. The fluid sample generally comprises a volume of less than about 1 ml. As an example, but without limitation, the volume of the fluid sample is about a drop of blood (e.g., 0.05 ml) or less. In accordance with embodiments of the present invention, the bridge is wetted by the fluid sample, to place the bridge and at least portions of the sample chamber in electrical contact with the multiple layer gel and in turn with the reference cell.

The substrate can comprise a dielectric material and may have a substantially planar surface. In accordance with embodiments of the present invention, the overlay may comprise a dielectric material. The overlay may be bonded or laminated to the substrate.

The leads generally comprise an electrically conductive material having a substantially continuous and/or uniform composition. More particularly, the leads may comprise a noble metal or other electrically conductive material. As an example, the leads may comprise an electrically conductive ink that is deposited on the substrate in a printing process. The one or more test leads generally extend from the sample chamber to a readout region, and the reference lead generally extends from the reference cell to the readout region. The readout region contains electrical contacts associated with the leads, and is generally adapted to operatively interconnect to the readout device and to form an electrical contact between the readout device and at least one test lead and the reference lead.

The multiple layer gel includes at least two layers. A first or isolation layer is in contact with the surface of the reference cell. In accordance with embodiments of the present disclosure, the isolation layer functions as a filter to block proteins and other unwanted molecules, preventing such molecules from coming into contact with the reference cell. Accordingly, the isolation layer may comprise a molecular weight screening layer that keeps large molecules away from the reference cell, but allows ions to flow through. Moreover, the filtering effect is not required to be absolute. For example, an isolation layer that slows the movement of proteins, such that the proteins are at least mostly prevented from coming into contact with the reference cell during the ORP measurement period can be provided. As an example, but without limitation, the isolation layer can be in the form of a gel comprising 4% agarose/1% hydroxyethyl cellulose (HEC) in purified water. The second layer of the multiple layer gel may comprise an electrolyte layer. The electrolyte layer generally covers the isolation layer. As an example, but without limitation, the electrolyte layer enables or facilitates an ionic and electrical connection between a sample placed in the test chamber of the test strip and the reference cell. In at least some embodiments, the electrolyte layer functions as a source of chloride ions. Where the electrolyte layer provides chloride ions, the potential of the sample can be determined with a relatively high level of precision, as the reference voltage of the reference cell is well known when the reference cell reacts with chloride ions. As an example, but without limitation, the electrolyte layer can be in the form of a gel that comprises 3% HEC in 3M KCl.

The reference cell generally provides a known voltage potential. Without limitation, the reference cell can comprise one of a silver/silver chloride half-cell, a copper/copper sulfate half-cell, a mercury/mercurous chloride half-cell, and a standard hydrogen half-cell.

The bridge is provided to establish electrical contact between a fluid sample in the sample chamber and the reference cell. The bridge can include an electrolytic solution, an ionic gel, a filter, or any water wicking or water transporting material, such as paper. The bridge is generally positioned between the sample chamber and the reference cell.

As previously noted, a filter can also be provided, as part of or in addition to the bridge. The filter generally functions to separate unwanted components or molecules of a fluid sample. For example, where the fluid sample is whole blood, the filter can operate to allow the plasma to travel across the bridge, to contact the reference cell via the multiple layer gel, while keeping non-plasma components of the whole blood from contacting the multiple layer gel and/or the reference cell. The filter can also operate by preventing red blood cells from contacting the working electrode. In accordance with at least some embodiments, the filter and bridge are formed from the same component. For example, the filter and bridge can be formed from the same piece of filter material. In embodiments in which the filter and bridge are integral to one another, a first portion of the integral component may comprise a filter portion, with a second portion comprising the bridge.

In practice, electrical contact is established between the leads when a suitable fluid sample is placed in the sample chamber, and the bridge is operative to place the fluid sample and the reference cell in electrical contact with one another. For example, where the bridge comprises a water transporting material, the bridge is operative to establish electrical contact between the fluid sample and the reference cell when the bridge is sufficiently wetted to establish an electrical contact with the reference cell and the fluid sample. Furthermore, an electrical circuit is established when a fluid sample is placed in the sample chamber 120 and two or more of the leads are operatively interconnected to the readout device.

In further aspects, the present disclosure provides a method for applying a multiple layer gel to a reference cell. More particularly, methods in accordance with embodiments of the present disclosure provide a protocol according to which a gel can be applied to a reference cell deposited on a substrate and/or other portions of a test strip that can be used for measuring the ORP of a fluid sample. The protocol includes applying a first or isolation layer comprising an agarose/hydroxyethyl cellulose and purified water solution to the half cell in an environment having an elevated temperature. As a particular example, 5 µL of a gel comprising 4% agarose/1% hydroxyethyl cellulose in purified water can be applied to a half cell having a diameter of about 4 mm. The gel comprising the isolation layer can be applied using a 65° C. heat block technique. The particular amount of material deposited as the isolation layer depends on the surface area of the reference cell. In particular, enough material should be provided so that the portion of the reference cell that is not in contact with the substrate is covered in its entirety. After initial application, the substrate can be removed from the heat, and allowed to dry at ambient temperature. After drying, the isolation layer forms a film covering the surface of the reference cell. As an example, the test strip can be allowed to dry at ambient temperature (i.e., room temperature) for about one hour. Next, a vacuum oven can be preheated to an elevated temperature. For example, the vacuum oven can be heated to a temperature of 65° C. An electrolyte layer is then applied over the isolation layer. The electrolyte layer can comprise 3% HEC in 3M KCl. Continuing the example of a reference cell having a diameter of about 4 mm, to which about 5 µL of solution comprising the isolation layer has been applied, about 10 µL of the electrolyte solution can be applied as the electrolyte layer. The test strip can then be placed in the preheated, 65° C. vacuum oven. The vacuum oven air vent should at this point be closed. The vacuum is then turned on, and the vacuum vent opened. The interior of the vacuum oven is pumped down to 0.02 MPa below atmospheric pressure, the vacuum vent is closed, and the vacuum is turned off. The test strip can then be heated under vacuum for a period of time. For example, the test strip can be heated in the vacuum oven for about 20 minutes. The air vent can then be opened and the test strip removed from the vacuum oven. After being allowed to cool, remaining manufacturing procedures required to complete the manufacture of the test strip can be completed.

Additional features and advantages of embodiments of the present disclosure will become more readily apparent from the following description, particularly when taken together with the accompanying drawings.

DETAILED DESCRIPTION

Figure 1:
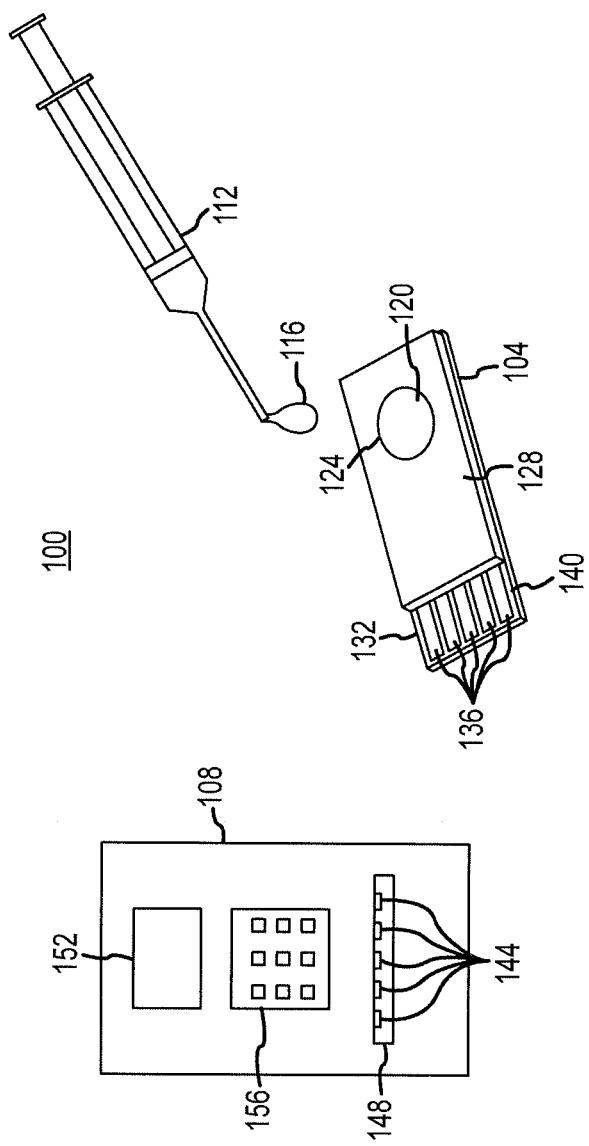
FIG. 1 depicts a system for measuring the oxidation-reduction potential of a fluid in accordance with embodiments of the present invention.

FIG. 1 depicts a system 100 for measuring the oxidation-reduction potential of a fluid sample in accordance with embodiments of the present invention. The system 100 generally includes a test strip 104 and a readout device 108. Also shown as a part of the system 100 is a fluid sample source 112 for supplying a fluid sample 116.

The test strip 104 generally includes a sample chamber 120. The sample chamber 120 may correspond to a test strip overlay aperture 124 formed in a test strip overlay 128. The test strip overlay 128 can be interconnected to a test strip substrate 132. A number of electrical contacts 136 are provided in a readout region 140. The electrical contacts 136 may be associated with various leads and other components of the test strip 104, as will be described in greater detail elsewhere herein.

The readout device 108 may include a set of readout device contacts 144. The readout device contacts 144 are generally configured to establish an electrical connection between the readout device 108 and the electrical contacts 136 of the test strip 104. As shown in the example system 100, the readout device contacts 144 may be associated with a readout aperture 148 that receives the readout region 140 of the test strip 104 when the test strip 104 is joined with the readout device 108 such that an electrical signal can be read from the electrical contacts 136 of the test strip 104 by the readout device 108. Alternatively, the readout device contacts 144 may comprise two or more flexible wires or leads that can be brought into contact with the electrical contacts 136 of the test strip 104.

In general, the readout device 108 comprises a voltmeter. More particularly, the readout device 108 operates to read a voltage between two readout contacts. Accordingly, the readout device contacts 144 operate to read an electrical potential or a voltage between any two of the electrical contacts 136 of the test strip 104. In accordance with further embodiments, the readout device 108 may perform a galvanostatic measurement, as described in greater detail elsewhere herein. In accordance with embodiments of the present invention, rather than providing five electrical contacts 136, a test strip 104 can include some other number of electrical contacts 136 including but not limited to two or three electrical contacts 136. The readout device 108 generally includes a sufficient number of readout device contacts 144 to operatively connect to a test strip 104. Moreover, the particular arrangement of readout device contacts 144 and/or readout aperture 148 can vary in order to accommodate different electrical contact 136 and readout region 140 arrangements of different test strips 104.

The readout device 108 may additionally include a user output 152. For example, the user output 152 can comprise a visual display for providing oxidation-reduction potential information regarding the fluid sample 116 to a practitioner.

Alternatively or in addition, the user output 152 can comprise a speaker or other source of audible output. In addition, a user input 156 may be provided to allow a practitioner to control aspects of the operation of the readout device 108.

In accordance with embodiments of the present invention, the fluid sample 116 may comprise blood or a blood product. For example, but without limitation, the fluid sample 116 can include human whole blood or plasma. The fluid sample source 112 can comprise any vessel or apparatus suitable for placing an appropriate volume of sample fluid 116 in the sample chamber 120 of the test strip 104. Accordingly, examples of a sample fluid source 112 include a syringe, a lancet, a pipette, a vial or other vessel or device.

Figure 2:
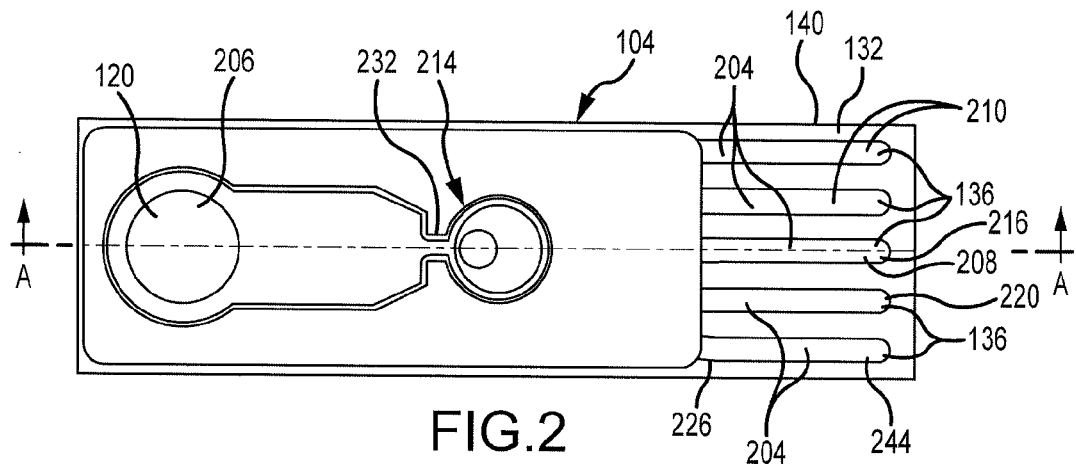
FIG. 2 illustrates a test strip in accordance with embodiments of the present invention in plan view.
Figure 3:
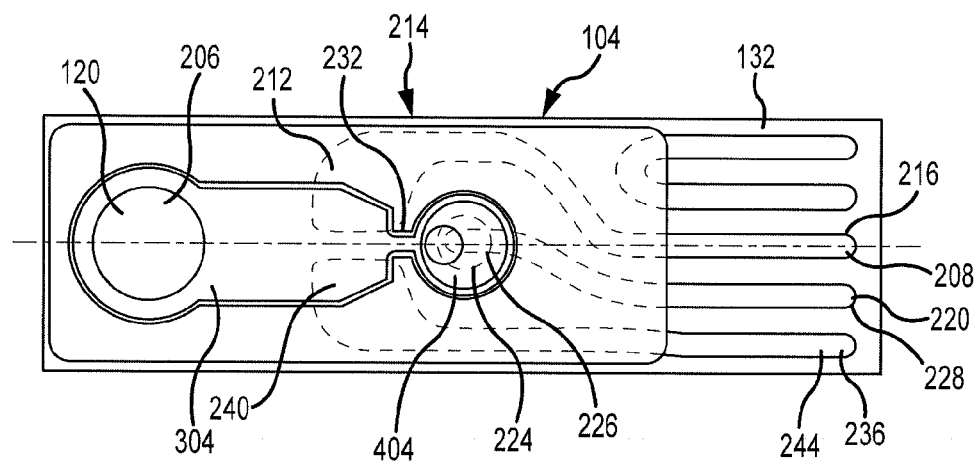
FIG. 3 illustrates the relationship of components in an assembled test strip in accordance with embodiments of the present invention.
Figure 4:
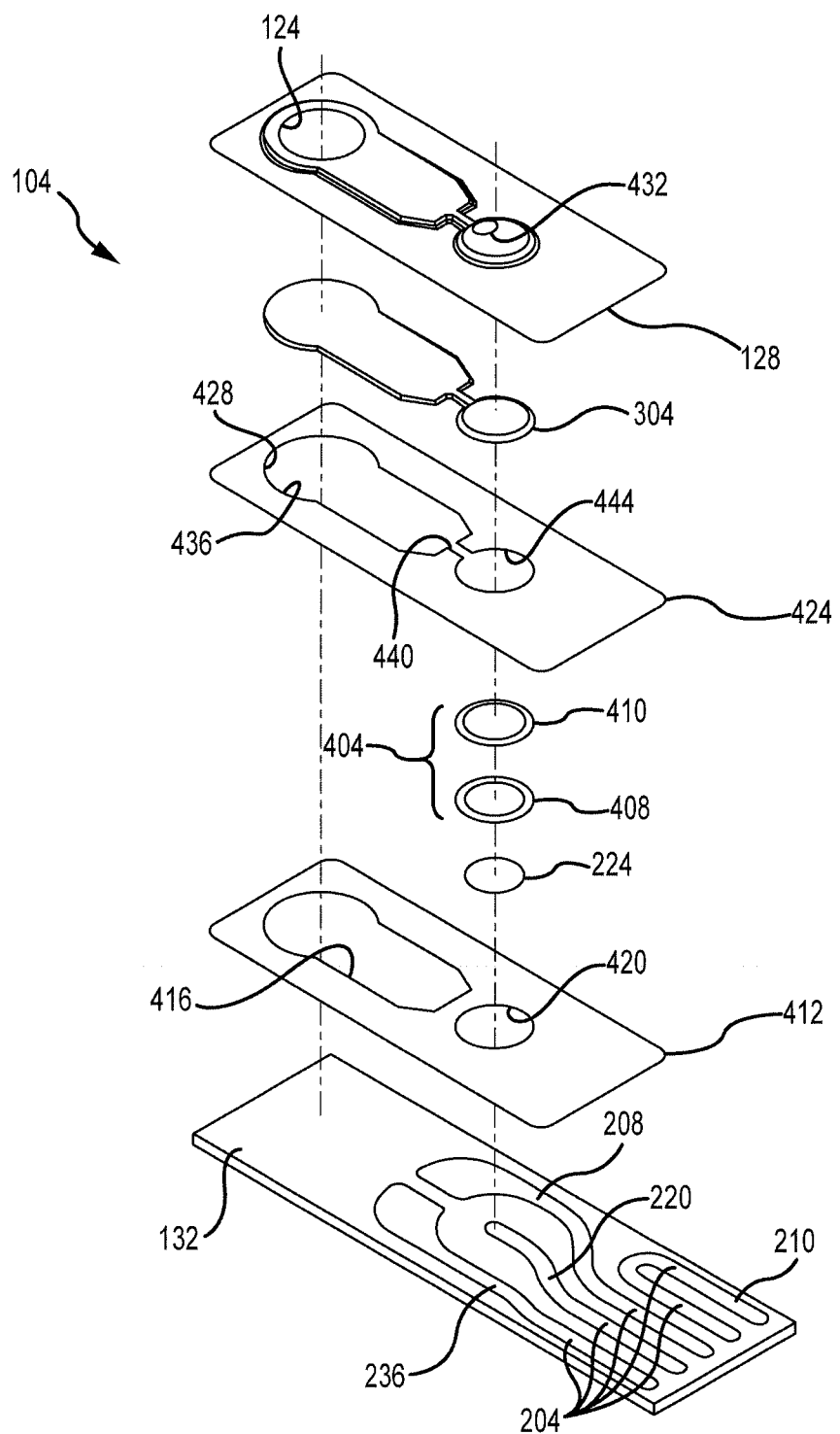
FIG. 4 is an exploded view of the test strip illustrated in FIGS. 2 and 3.

FIG. 2 illustrates a test strip 104 in accordance with embodiments of the present disclosure in top plan view, FIG. 3 illustrates components of the test strip 104 of FIG. 2 that lie behind other components using dotted lines, and FIG. 4 illustrates the test strip 104 in an exploded view. In general, the substrate 132 carries and/or has formed thereon a number of electrically conductive leads 204 that terminate in the test strip readout contacts 136. The substrate 132 itself may comprise a dielectric material. For example, the substrate 132 may comprise a ceramic material. Moreover, the substrate 132 may comprise a substantially planar surface on which various components of the test strip 104 may be interconnected or formed. In accordance with further embodiments, the test strip 104 substrate 132 may comprise or have formed thereon a depression or well 206 in an area corresponding to the sample chamber 120 of the test strip 104. In accordance with still other embodiments of the present disclosure, the surface of the substrate 132 is entirely flat.

At least one of the leads 204 is a first test lead or working electrode 208 that extends between a first area 212 (see FIG. 3) corresponding to or within a test cell area 214 of the test strip 104 and a second area 216 corresponding to the readout contact 136 of the working electrode 208. In accordance with embodiments of the present invention, at least the first area 212 of the working electrode 208 is formed from an electrically conductive material having a substantially continuous and/or uniform composition. It should be understood that, as used herein, a substantially continuous and/or uniform composition means that the material comprising the working electrode 208 has the same chemical composition and/or a molecular structure at any point in a cross section of a portion of the working electrode 208 as at any other point in the cross section of the working electrode 208. More particularly, in such embodiments the electrically conductive material of the working electrode 208 is not coated or substantially not coated by a substance selected to chemically interact with respect to the sample fluid 116.

As examples, and without necessarily importing limitations into the claims, the working electrode 208 may comprise an electrically conductive ink deposited on the substrate 132 in a printing operation. In accordance with further exemplary embodiments, the working electrode 208 may comprise an electrically conductive layer that is sputtered on the substrate 132, or that is laminated or otherwise joined to the substrate 132.

A test strip 104 in accordance with embodiments of the present disclosure additionally includes a lead 204 comprising a reference lead or electrode 220. The reference lead 220 generally extends between a first portion 226 in electrical contact with a reference cell 224 and a readout region 228 of the reference lead. In accordance with exemplary embodiments of the present invention, the reference lead 220 may be formed using the same or similar process and/or material as the working electrode 208.

A test strip 104 in accordance with embodiments of the present disclosure may also include a second test lead or counter electrode 236. The counter electrode 236 may be formed from a substantially continuous or uniform electrically conductive substance that extends from a first area 240 that corresponds to or lies within the test cell area 214, to a second area 244 corresponding to the readout portion 136 of the counter electrode 236. The counter electrode 236 may be formed using the same or similar process and/or material as the working electrode 208 and the reference electrode 220.

The reference cell 224 is selected to provide a stable, well-known voltage potential. More particularly, the reference cell 224 may comprise a reference electrode that operates as a half cell as part of an electrochemical cell that is completed with the addition of a sample fluid to the sample chamber 120 as described herein. As can be appreciated by one of skill in the art after consideration of the present disclosure, by providing a reference cell 224 with a well known voltage, the potential of the other half of the cell (i.e., of the fluid sample) can be determined. This in turn allows the ORP of the sample fluid 116 to be determined, as described herein. For example, but without limitation, the reference cell 224 may comprise a silver/silver chloride electrode, copper/copper sulfate electrode, mercury/mercurous chloride, standard hydrogen electrode, calomel electrode, or other electrochemical reference half-cell.

A bridge 232 extends between the reference cell 224 and the sample chamber 120. In accordance with embodiments of the present invention, the bridge 232 may comprise a filter. For example, the bridge 232 may be formed from paper, fiberglass, or other filter media. As can be appreciated by one of skill in the art after consideration of the present disclosure, when a fluid sample 116 is placed in the sample chamber 120, the bridge 232 is wetted, establishing an electrically conductive bridge between the fluid sample 116 in the sample chamber 120 and the reference cell 224.

The bridge 232 can be provided as part of a filter element 304. The filter element 304 is generally positioned such that a fluid sample 116 placed in the sample chamber 120 must pass through or across the filter element 304 in order to enter the test cell area 214. Accordingly, the filter element 304 can comprise a filter media that extends across the sample chamber 120, and that continues through the bridge portion 232, to the test cell area 214. In accordance with other embodiments, the filter element 304 can be interposed between the sample chamber 120 and the test cell area 214. In accordance with still other embodiments, the filter element 304 can be limited to the bridge portion 232. As can be appreciated by one of skill in the art after consideration of the present disclosure, a filter element 304 can provide a transport medium for moving portions and/or components of a fluid sample 116 from the sample chamber 120 to the test cell area 214. In accordance with at least some embodiments, the filter element 304 can also prevent certain components of a fluid sample 116 from entering the test cell area 214. For instance, where the sample fluid 116 comprises whole blood, the filter element 304 can allow plasma to enter the test cell area 214, while preventing red blood cells, platelets, and other components of whole blood from entering the test cell area 214.

Figure 5:
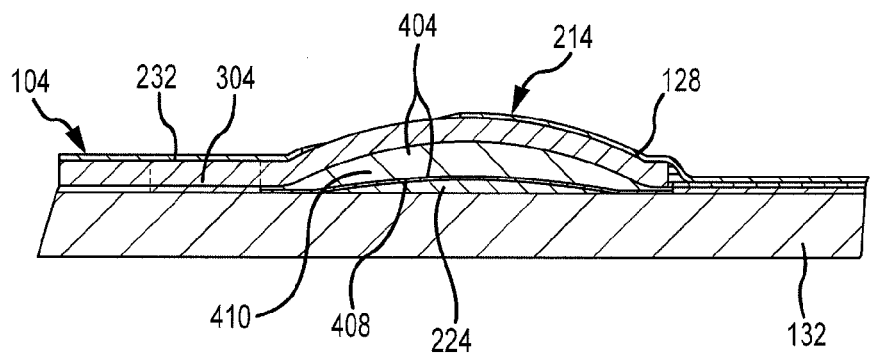
FIG. 5 is a partial cross-section of the test strip illustrated in FIGS. 2 and 3.

As shown in FIG. 4, illustrating a test strip 104 in accordance with embodiments of the present disclosure in an exploded view, and in FIG. 5, illustrating the test cell area 214 of a test strip 104 in accordance with embodiments of the present disclosure in cross-section, the reference cell 224 is covered by a multiple layer gel 404. In particular, a first or isolation layer 408 is placed directly on top of the reference cell 224, covering those portions of the reference cell 224 that are not in contact with the substrate 132 and/or an electrically conductive lead 204. In accordance with embodiments of the present disclosure, the isolation layer 408 is a very thin layer that prevents proteins and other molecules from contacting the reference cell 224. In accordance with at least some embodiments of the present disclosure, the isolation layer comprises 4% agarose and 1% hydroxyethyl chloride (HEC) dissolved in purified water. The purified water may comprise ultra purified water, deionized water and/or filtered water. Purification can be through various processes, including but not limited to, reverse osmosis, filtration, ultraviolet oxidation, and/or electro dialysis. For example, the water may be characterized as high-performance liquid chromatography (HPLC) grade water, and/or 18 MOhm/cm water.

As can be appreciated by one of skill in the art after consideration of the present disclosure, absent the presence of a suitable fluid sample 116 in the sample chamber 120, the various leads 204 are not in electrical contact with one another. In particular, electrical contact between portions of the leads 204 in the test cell area 214 is not established until a suitable fluid sample 116 is placed in the sample chamber 120, and the bridge 232 has been sufficiently wetted to place the reference lead 220 into electrical contact with the working electrode 208 and/or the counter electrode 236 through the fluid sample 116.

The substrate 132 may comprise a ceramic, a fiber or polymer that is sufficiently rigid to provide mechanical support for the subsequent layers. The electrically conductive leads 204 are supported by the substrate 132. As an example, and without limitation, the conductive leads 204 can be deposited on the surface of the substrate 132 by, for example, a sputtering, printing, etching, stenciling, or plating process. The electrically conductive leads 204 may be formed from any electrically conductive material. Examples of suitable electrically conductive materials include platinum, gold, indium, electrically conductive ink, and doped carbon. The conductive leads 204 can be formed in various patterns. In general, the conductive leads 204 include a working electrode 208, a reference electrode 220 and a counter electrode 236. The leads 204 can also include leads 210 that can be used by the readout device 108 to sense the presence and/or identity of a test strip 104.

The reference cell 224 can be placed on the barrier layer substrate 132, with at least some of the reference cell 224 positioned over and/or in contact with a portion of the reference lead or electrode 220. A dielectric or mask layer 412 may be placed over or formed on portions of the substrate, and covering at least portions of the electrically conductive leads 204. For example, the dielectric layer 412 can cover portions of the various electrically conductive leads 204, while leaving portions of the electrically conductive leads 204 within a readout region 140 of the test strip 104 uncovered. In addition, the dielectric layer 412 can include a first aperture 416 that defines at least a portion of the sample chamber 120, and that leaves at least portions of a first area 212 of the working electrode 208 and a first area 240 of the counter electrode 236 uncovered and exposed to the sample chamber 120 volume. The dielectric layer 412 can additionally include a second aperture 420. The second aperture 420 can correspond to the reference cell 224 and/or the protective multiple layer gel 404. As an example, the dielectric layer 412 may be formed from a dielectric film, or a deposited (e.g., a printed) dielectric material.

A spacer layer 424 is interconnected to the dielectric layer 412. The spacer layer 424 includes a spacer layer aperture 428. The spacer layer aperture 428 may have an area that is the same as or larger than an area of the filter 304. Accordingly, the spacer layer aperture 428 can define the perimeter of a volume that is entirely or substantially occupied by the filter 304. Moreover, the spacer layer aperture can include a first portion 436 that defines at least portions of the sample chamber 120, a second portion 440 corresponding to the bridge 232, and a third portion 444 providing a volume that is at least partially occupied by the reference cell and/or the multiple layer gel 404.

As shown, the filter 304 can extend from the an area encompassing at least part of the first aperture 416 and the sample chamber 120, through the bridge 232 area, to the second aperture 420 of the dielectric layer 412. The filter 304 can function, when wetted, as a bridge 232 to electrically connect a portion of a sample 116 within the sample chamber 120 to the reference cell 224, through the multiple layer gel 404.

A test strip overlay 128 can be interconnected to the spacer layer 424. The test strip overlay 128 generally includes an overlay aperture 124. The overlay aperture 124 allows a fluid sample 116 to be placed into the sample chamber 120 of the test strip 104.

The test strip overlay 128 can additionally include a vent aperture 432. As can be appreciated by one of skill in the art after consideration of the present disclosure, the vent aperture 432 can facilitate the transfer of fluid from an area of the sample chamber 120 adjacent the overlay aperture 124 to the test cell area 214 by preventing a vapor lock from forming in the sample chamber 120. As shown, the test strip overlay 128 can be formed from multiple layers. Moreover, layers beneath a top layer can provide features that increase the size of the sample chamber 120, the bridge 232 area, and/or the test cell area 214. Accordingly, the test strip overlay 128 can itself comprise a laminated structure that cooperates with the spacer layer 424 to define portions of the sample chamber 120 the bridge 232 area, and/or the test cell area 214. In accordance with still other embodiments, the test strip overlay 128 can comprise a layer with no features other than the overlay aperture 124 and a vent aperture 432.

With reference now to FIG. 5, a cross-section of the test strip 104 in elevation, taken along section line A-A in FIG. 2 and including the test cell area 214, is shown. The reference cell 224 has a first surface placed directly on the substrate 132. As best shown in FIG. 3, the reference cell 224 is positioned over at least a first portion 226 of the reference lead 220, such that the reference cell 224 is an electrical contact with the reference lead 220. The first or isolation layer 408 the multiple layer gel 404 is placed over the exposed surface of the reference cell 224 (i.e. the surface of the reference cell 224 that is not in direct contact with the substrate 132 and/or the reference lead 220). In accordance with embodiments of the present disclosure, the first layer 408 forms a thin film over the otherwise exposed surface of the reference cell 224. The second or electrolyte layer 410 of the multiple layer gel 404 is placed over the first layer 408. As shown, the second layer 410 can occupy a larger portion of the test cell area 214 than does the first layer 408. Extending into the test cell area 214 is the filter 304. In particular, as shown with dotted lines, the bridge portion 232 of the filter 304 is shown, with the test cell area 214 portion of the filter 304 to the right in the figure, and the sample chamber portion of the filter 304 (partially shown in FIG. 5) to the left in the figure. Also visible in the figure is a portion of the test strip overlay 128, and the vent aperture 432.

In accordance with embodiments of the present disclosure, the various layers of the test strip 104, such as the substrate 132, the dielectric layer 412, the spacer layer 424, and the test strip overlay 128 can be adhered or bonded to one another to form a laminated structure, with other elements, such as the electrically conductive leads 204, the half cell 224, and the multiple layer gel 404 deposited on the substrate 132 and/or other components of the test strip 104. The filter 304 can be adhered to the substrate 132 or other components, and/or can simply be trapped within the volume defined by at least the substrate 132 on a bottom, the spacer layer 424, and the overlay 128.

In accordance with embodiments of the present invention, at least some, if not most or all, of the leads 204 are formed by printing an electrically conductive material. Non-limiting examples of electrically conductive materials are carbon (such as carbon black, carbon nanotubes, graphene sheets, graphite and bucky balls), metallic materials (such as powder forms of copper, silver, gold and other known conductive metallic materials) and conductive polymers. Furthermore, the conductive material can be printed in the form of a substantially continuous and/or uniform composition, as described above. In accordance with further embodiments, the leads 204 are formed by sputtering gold, platinum, or some other metal.

The test strip 104 forms an electrochemical test cell. In particular, when a blood sample has been placed in the sample cell 120, for example through the test strip overlay layer 128 aperture 124, the electrochemical test cell comprises the separated plasma, contained within the sample chamber 120 and wetting the filter 304, the multiple layer gel 404, and the reference cell 224. The electrical potential of the test cell can then be read by interconnecting at least one of the working electrode 208 and counter electrode 236, and the reference lead 220 to a readout apparatus or device 108.

Figure 6:
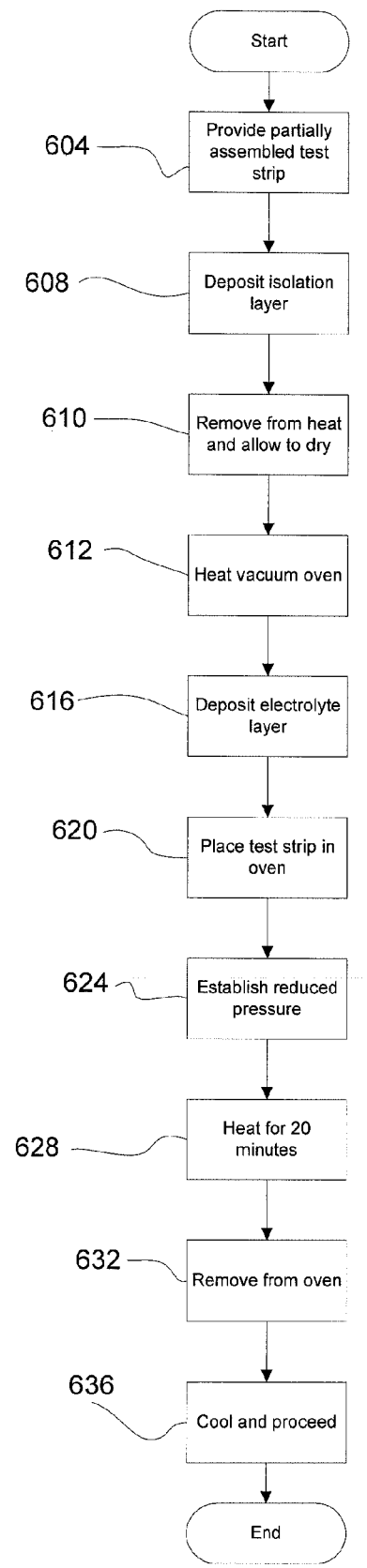
FIG. 6 is a flowchart depicting aspects of a process for forming a multiple layer gel over a reference cell in accordance with embodiments of the present disclosure.

With reference now to FIG. 6, a flowchart illustrating aspects of a process for forming a multiple layer gel 404 over a reference cell 224 in accordance with embodiments of the present disclosure is shown. Initially, at step 604, a partially assembled test strip 104, comprising at least the substrate 132 with test leads 204 formed thereon, and with the reference cell 224 in place on the substrate 132 and in contact with the reference lead 220, is provided.

Next, the isolation layer 408 is applied over the reference cell 224 (step 608). The isolation layer 408 covers the surface of the reference cell 224 that is not in contact with the substrate 132 and/or the reference lead 220. The material used to form the isolation layer 408 is selected to act as a molecular weight screening layer. More particularly, the isolation layer 408 is formed from a material selected to keep large molecules, such as but not limited to proteins, from contacting the reference cell 224, at least during a time period in which ORP or other measurements are being taken. Moreover, the isolation layer 408 is a material that allows ions to flow through the isolation layer 408 and to contact the reference cell 224. As an example, but without limitation, the isolation layer 408 may be deposited as a gel that comprises agarose and hydroxyethyl cellulose (HEC) dissolved in water. The agarose and HEC may be provided in about a 4:1 ratio. Moreover, the water may comprise ultrapure water. In accordance with at least some embodiments, the isolation layer 408 may be provided as a gel comprising 4% agarose and 1% HEC in purified water. Where the reference cell 224 is about 4 mm in diameter, about 5 μL of the 4% agarose and 1% HEC and dissolved water gel can be deposited over the reference cell 224. As another example, again without limitation, the isolation layer 408 can be provided as a gel comprising 2% agarose and 0.5% HEC in the purified water, with about 10 μL of the gel deposited over the 4 mm diameter reference cell 224. In accordance with at least some embodiments, the gel comprising the isolation layer 408 is deposited over the reference cell 224 using a 65° C. heat block technique. The partially completed test strip 104 can then be removed from the heat, and the isolation layer 408 is allowed to dry for about one hour at ambient temperature (step 610). At step 612, which can be performed while the isolation layer 408 is drying, a vacuum oven is heated to 65° C.

The electrolyte layer 410 can then be applied over the isolation layer 408 (step 616). In accordance with embodiments of the present disclosure, the isolation layer 408 provides a source of ions, to facilitate an ionic/electrical connection between a sample fluid 116 wetting the filter 304 and the reference cell 224. As an example, but without limitation, the electrolyte layer 410 can be provided as a gel comprising 3% HEC in 3M KCl. Continuing the previous example in which the reference cell 224 occupies a disk shaped area having a diameter of about 4 mm, about 10 μL of the gel comprising the isolation layer 408 can be deposited over the isolation layer 408. At step 620 the partially completed test strip 104 can be placed in the preheated 65° C. vacuum oven, the air vent on the vacuum oven is closed, the vacuum is turned on, and the vacuum vent is opened. The vacuum oven chamber is then pumped down to about 0.02 MPa below atmospheric pressure, the vacuum vent is closed, and the vacuum is turned off (step 624). The partially completed test strip 104 is then heated under vacuum for about 20 minutes (step 628). At step 632 the air vent is opened, and the partially completed test strip 104 is removed from the vacuum oven. The partially completed test strip 104 is then allowed to cool (step 636), e.g. about 10 minutes, before proceeding to the next manufacturing steps, such as the addition of the mask layer 412, spacer layer 424, filter 304, and overlay 128.

As can be appreciated by one of skill in the art after consideration of the present disclosure, the procedure for applying the multiple layer gel 404 over the reference cell 224 can be controlled so as to obtain consistent results. For example, the multiple layer gel 404 can be dried under conditions that limit or reduce the formation of microcracks or other discontinuities. Accordingly, drying the layers of the multiple layer gel 404 can be performed at ambient temperatures and pressures, while applying heat, in a vacuum, and the like. Alternatively or in addition, different gel layer compositions can be used. For example, a gel comprising a hydroxyethyl cellulose material can be mixed with a polymer to promote consistency of one or more layers of the multiple layer gel 404 in finished test strips 104. As described herein, a first or isolation layer 408 can be formed directly over the reference cell 224. As an example, this first layer can comprise a water based gel containing about 4% agarose and about 1% hydroxyethyl cellulose. This first layer generally forms a thin film over the reference cell 224. Moreover, this composition is relatively resistant to cracking. A second, salt containing layer 410 can be formed over the first layer. The second layer 410, for example, can comprise a water based gel containing about 3% hydroxyethyl cellulose and about a 3M concentration of KCl. As used herein, an amount is "about" a stated value if it is within ±10% of the stated value. As an example, but without limitation, 5 μL of the first layer 408 may be placed over the reference cell 224, and 104, of the second layer 410 may be placed over the first layer 408, after the first layer 408 has been allowed to dry for from about 1 to about 2 hours at ambient temperature. The second layer 410 can be allowed to dry for about 8 to about 12 hours at ambient temperature. As can be appreciated by one of skill in the art after consideration of the present disclosure, this second layer 410 provides a source of ions to complete an ionic and/or electrical connection between a sample fluid 116 or component of a sample fluid 116 and the reference cell 224. Moreover, the ions provided by the second layer 410 can be selected such that the reference cell 224 creates a barrier between the reference cell 224 and the protein within a fluid sample 116 that has been placed in the sample chamber 120 and that has been transported to the vicinity of the gel 708 and the reference cell 224 by the filter 304. This barrier need not be absolute. Instead, the barrier should persist long enough to allow a measurement to be completed or at least largely completed before any proteins from the fluid sample contact the reference cell 224.

Figure 7:
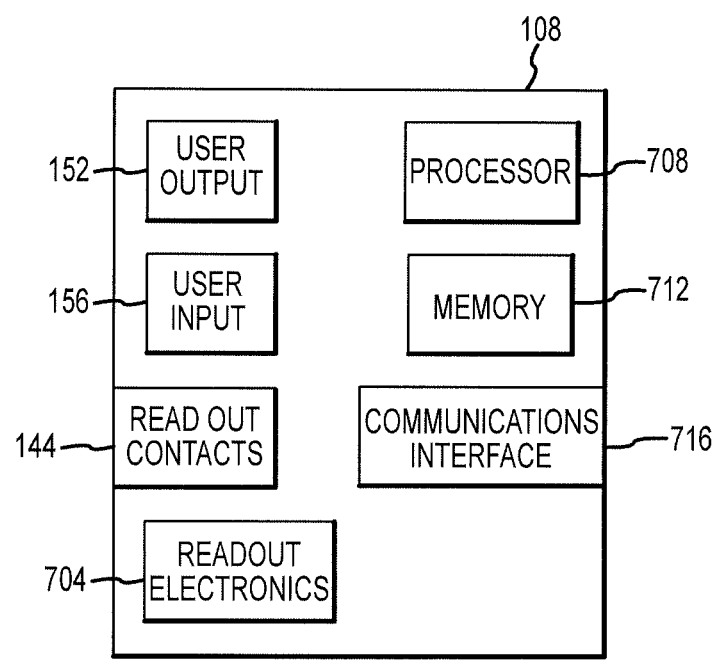
FIG. 7 is a block diagram depicting components of a readout device in accordance with embodiments of the present disclosure.

FIG. 7 is a block diagram depicting components of a readout device 108 in accordance with embodiments of the present invention. In general, the readout device 108 includes a plurality of readout device contacts 144. The readout device contacts 144 may be associated with a receiving structure, such as the aperture 148 illustrated in FIG. 1, for mechanically interconnecting the readout device 108 to a test strip 104, to facilitate an electrical interconnection between at least two readout device contacts 144 and at least two electrical contacts 136 of the test strip 104. Alternatively or in addition, the readout device contacts 144 may comprise conductive leads or probes that can be selectively placed into contact with electrical contacts 136 of a test strip 104.

The readout device 108 also includes or comprises a voltmeter or readout electronics portion 704. As can be appreciated by one skilled in the art, the readout electronics 704 can be implemented in various ways. For example, the readout electronics 704 may comprise a galvanostat. As another example, the endpoint electronics may comprise a potentiostat. As a further example, the readout electronics 704 may comprise a digital voltmeter that includes an integrating converter. In accordance with further embodiments, the readout electronics 704 can comprise an analog voltmeter or a digital or analog null balance voltmeter.

A processor 708 that includes and/or is associated with memory 712 can be provided for controlling various aspects of the operation of the readout device 108. The processor 708, for example executing instructions stored in memory 712, can implement a process according to which the voltage between the working electrode 208, the counter electrode 236, and/or the reference electrode 220 is monitored over time by the readout electronics 1304. Moreover, this voltage can be monitored while the readout electronics 704 applies a current across at least the counter electrode 236 and the working electrode 208. The processor 708 can further operate to calculate and cause to be displayed a readout indicative of the oxidation-reduction potential of a fluid sample 116 held in the sample chamber 120 from the voltage read by the readout electronics 704.

For providing information regarding the determined oxidation-reduction potential of a fluid sample 116 in the sample chamber 120 to a user, a user output 152 is provided. The user output 152, can, in an exemplary embodiment, comprise a digital output that displays an oxidation-reduction potential value. Alternatively or in addition, the user output 152 can include indicator lamps, an analog output, or other visual output. In accordance with still further embodiments, the user output 152 can include an audible output, such as a selected tone or sequence of tones or machine-generated speech.

A user input 156 can be included for receiving control information from a user. For example, the user input 156 may receive input to power on or power off the readout device 108, to perform diagnostics related to the proper operation of the readout device 108, to receive input regarding various operating parameters, or other user input. As examples, the user input 156 can include buttons, switches, keypads, and/or a touch screen interface integrated with a visual display, such as may be included in the user output 152.

The readout device 108 may additionally include a communications interface 716. The communications interface 716, if provided, may support interconnections between the readout device 108 and other systems or devices. For example, the communications interface 716 may comprise a wired or wireless Ethernet connection, a universal serial bus port, or an IEEE 1394 port for interconnecting the readout device 108 to a personal computer or computer network.

In addition, although an exemplary readout device 108 comprising a dedicated standalone device that may or may not be interconnected to other devices has been described, embodiments of the present invention are not so limited. For example, a readout device 108 in accordance with embodiments of the present inventions may be implemented as a standard voltmeter. In accordance with other embodiments, the readout device 108 may comprise an electrical test or diagnostic system, such as a user configurable potentiostat and/or galvanostat operated alone or in combination with a personal computer. In accordance with still other embodiments, a readout device 108 may be implemented as a personal computer running suitable programming and providing an interface capable of sensing a voltage between a working electrode 208 and a reference electrode 220 of a test strip 104.

Figure 8:
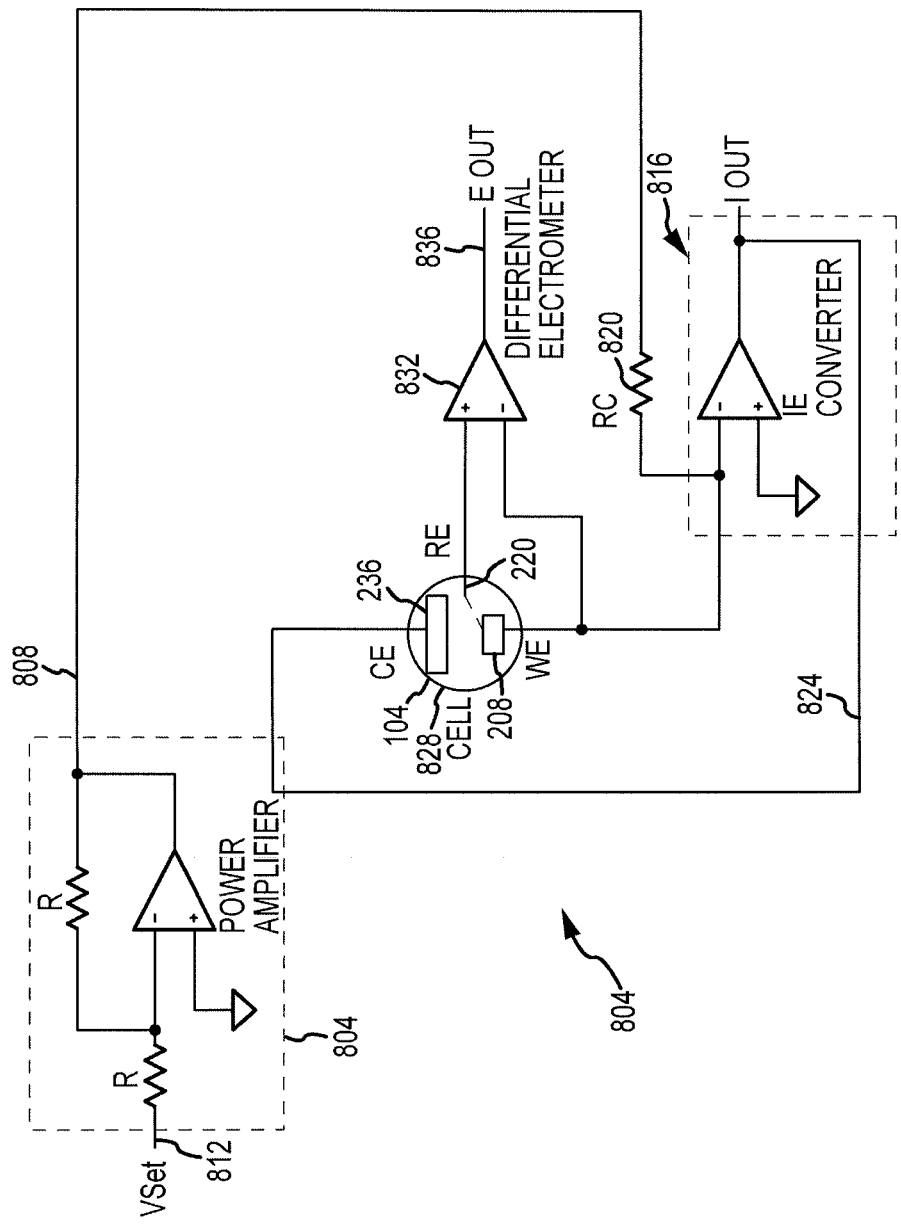
FIG. 8 depict components of readout electronics and an interconnected test strip in accordance with embodiments of the present disclosure.

FIG. 8 depicts components of a readout device 108 operatively interconnected to a test strip 104 in accordance with embodiments of the present invention. More particularly, features of a voltmeter or readout electronics portion 704 of a readout device 108 interconnected to a test strip 104 containing a fluid sample 116 are depicted. As can be appreciated by one of skill in the art after consideration of the present disclosure, the test strip 104 containing a fluid sample 116 comprises an electrochemical cell 828. The electrochemical cell 828 includes the fluid sample 116, the multiple layer gel 404, and the reference cell 224. Moreover, the fluid sample 116, for example by wetting a bridge 232 and/or filter 304, places portions of the working electrode 208, reference electrode 220, and counter electrode 236 in electrical contact with one another.

In general, the readout electronics 704 include a power amplifier 804. The output 808 from the power amplifier 804 comprises a current having a set point determined by the voltage $V_{set}$ 812 provided as an input to the power amplifier 804. The output current 808 from the power amplifier 804 is passed to a current-potential (IE) converter 816. The current 808 from the power amplifier 804 can be supplied via a resistor 820 to the negative input of the IE converter 816. The IE converter 816 in turn supplies an output current 824 that is provided to the counter electrode 236. The negative input of the IE converter 816 is additionally connected to the working electrode 208. As can be appreciated by one of skill in the art after consideration of the present disclosure, the resistance between the counter electrode 236 and the working electrode 208 can vary, depending on the composition and characteristics of a fluid sample 216 placed in the test strip 104. However, the power amplifier 804 and the IE converter 816, in combination, provide a constant current that is supplied to the counter electrode 236, and that is passed through the electrochemical cell 828.

While the current is applied across the counter electrode 236 and the working electrode 208, the voltage potential between the working electrode 208 and the reference electrode 220 is monitored by a differential amplifier or electrometer 832. More particularly, the differential amplifier 832 provides a voltage output 836 that is indicative of the oxidation-reduction potential of the sample 116 placed within the sample chamber 120. This voltage output 836 can be presented to a user, for example through the output 152 of the associated readout device 108.

Figure 9:
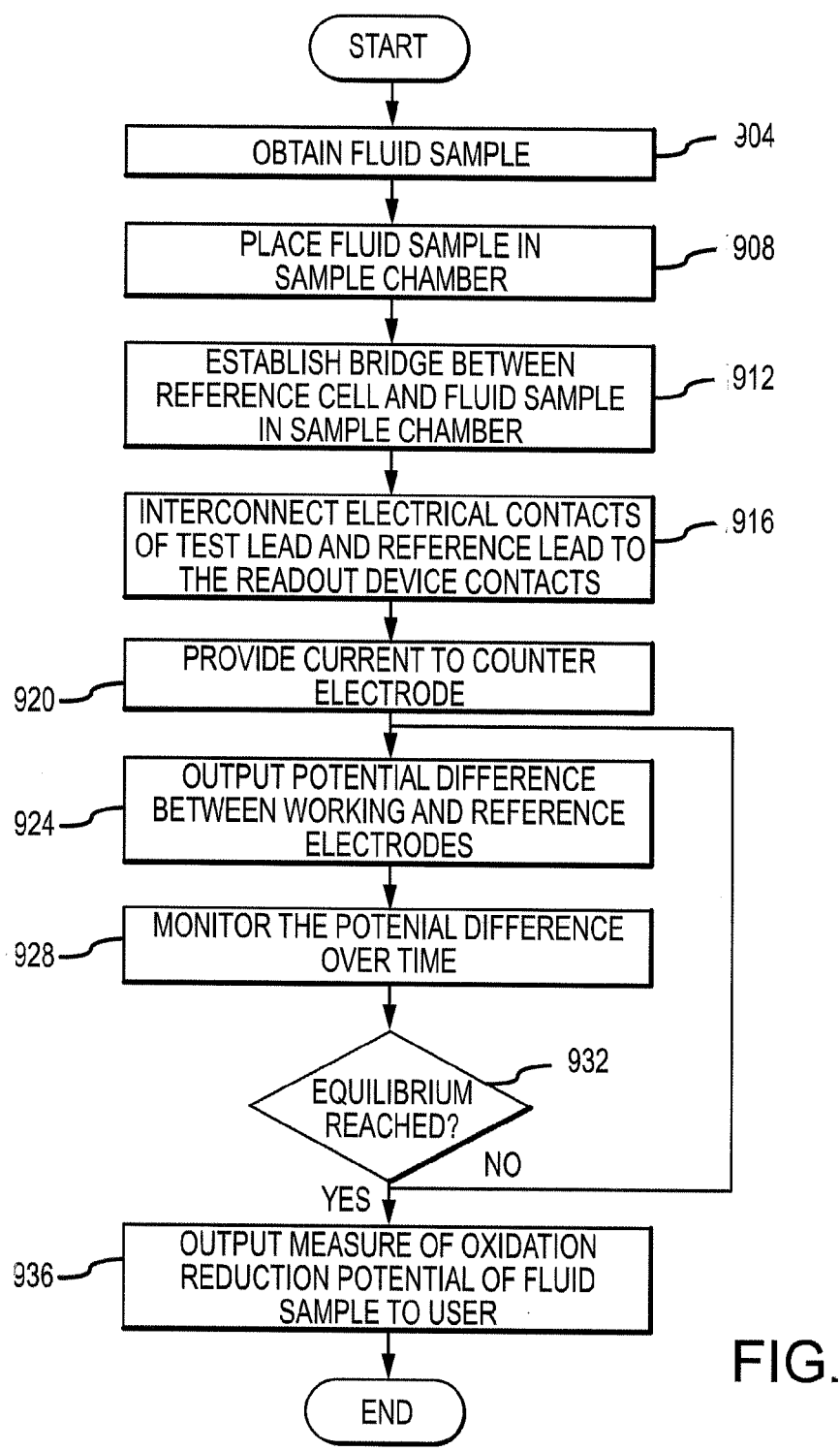
FIG. 9 is a flowchart depicting aspects of a process for measuring the oxidation-reduction potential of a fluid sample in accordance with embodiments of the present disclosure.

With reference now to FIG. 9, aspects of a method for measuring the oxidation-reduction potential (ORP) of a sample fluid 116 are illustrated. In general, the method includes steps of obtaining a fluid sample 116 (step 904), placing the fluid sample 116 in the sample chamber 120 of a test strip 104 (step 908), and establishing an electrically conductive bridge 232 between the reference cell 224 and the sample chamber 120 of the test strip 104, for example by wetting a filter 304 with the sample fluid 116 (step 912). At step 916, the working electrode 208, reference electrode 220, and counter electrode 236 are interconnected to readout device contacts 144. For example, the counter electrode 236 can be interconnected to the current output 824 of the readout electronics 704, the working electrode 208 can be connected to the negative inputs of the IE converter 816 and the differential electrometer 836 of the readout electronics 704 and the reference electrode 220 can be interconnected to an input of the differential amplifier 832. The readout electronics 704 are then operated to provide a current that is passed across the reference cell 828, between the counter electrode 236 and the working electrode 208 (step 920). As examples, and without limitation, the amount of current passed between the counter electrode 236 and the working electrode 208 by the readout electronics 704 can be from about $10^{-12}$ amps to about $10^{-9}$ amps. In accordance with further embodiments, the magnitude of the current passed through the electrochemical cell 828 can be from about $1\times10^{-14}$ amps to about $1\times10^{-6}$ amps. As further examples, the applied current can be varied over time. For instance, a step function can be followed, according to which the applied current changes after some point of time from a first value (e.g., $10^{-9}$ amps) to a second value (e.g., $10^{-11}$ amps). While the current is applied between the counter electrode 236 and the working electrode 208, the potential difference between the working electrode 208 and the reference electrode 220 is provided as the output 836 of the differential amplifier 832 (step 924).

The output 836 from the differential amplifier 832 can be monitored over time (step 928). At step 932, a determination can be made as to whether equilibrium has been reached. The determination that equilibrium has been reached can include monitoring the rate of change in the output signal 836 of the differential amplifier 832, until that rate of change has dropped to a predetermined level. Alternatively, the output voltage 836 can be measured at different points in time, and a linear or curved representation of the change in the voltage output 836 can be used to arrive at an oxidation-reduction potential reading. If equilibrium has been reached, the determined oxidation-reduction potential value is presented to a user of the readout device 108 (step 936). For example, the determined oxidation-reduction potential value can be presented as a measured voltage. If equilibrium has not been reached, the process can return to step 920. Moreover, for at least most of the time that the potential difference is being measured as part of determining an ORP value, the multiple layer gel 404 prevents proteins in the fluid sample 116 from corrupting the measured value. After the ORP value has been output, the process can end.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. An oxidation-reduction potential test device, comprising:
   a substrate;
   a spacer layer interconnected to at least a portion of the substrate, wherein the spacer layer defines a sample chamber;
   a test strip overlay, wherein the test strip overlay is interconnected to at least a portion of the spacer layer;
   a first test lead supported by the substrate, the first test lead including:
      a first area extending into the sample chamber;
      a second area extending from the sample chamber to a readout region;
   a second test lead supported by the substrate, the second test lead including:
      a first area extending into the sample chamber;
      a second area extending from the sample chamber to a readout region;
   a reference cell;
   a reference lead, including:
      a first area in electrical contact with the reference cell;
      a second area extending from the reference cell to a readout region;
   a filter, wherein at least a portion of the filter overlaps at least a portion of each of the first area of the first test lead, the first area of the second test lead, and the first area of the reference lead; and
   a gel volume, wherein the gel volume includes a first layer in contact with the reference cell and a second layer over the first layer, wherein the first layer differs in composition from the second layer, wherein the first layer comprises an agarose and hydroxyethyl cellulose layer, and wherein the second layer comprises an agarose and KCl layer.

2. The device of claim 1, wherein at least a portion of the first test lead, the reference cell, at least a portion of the reference lead, and a bridge are between the substrate and the overlay when the overlay is interconnected to the substrate, wherein the overlay includes an aperture, wherein the aperture corresponds to at least a portion of the sample chamber when the overlay is interconnected to the substrate, wherein the filter is at least partially contained within the sample chamber, and wherein the gel volume is in communication with the sample chamber.

3. The device of claim 1, wherein the reference cell includes a silver/silver chloride reference cell.

4. The device of claim 1, further comprising:
   a fluid sample, wherein the fluid sample comprises a wetting agent that wets the filter that electrically interconnects the first area of the first test lead, the first area of the second test lead, and the first area of the reference lead.

5. The device of claim 4, wherein the fluid sample is whole blood.

6. The device of claim 1, wherein the first test lead, the second test lead, and the reference lead are formed from an electrically conductive material having a constant composition.

7. The device of claim 6, wherein the electrically conductive material having a constant composition is platinum.

8. The device of claim 1, wherein the first test lead, the second test lead, and the reference lead are accessible to a test device in the readout region when the overlay is interconnected to the substrate.

9. The device of claim 1, wherein the first test lead, the second test lead, and the reference lead are located on a common plane.

10. An oxidation-reduction potential test device, comprising:
a substrate;
a spacer layer interconnected to at least a portion of the substrate, wherein the spacer layer defines a sample chamber;
a test strip overlay, wherein the test strip overlay is interconnected to at least a portion of the spacer layer;
a first test lead supported by the substrate, the first test lead including:
a first area extending into the sample chamber;
a second area extending from the sample chamber to a readout region;
a second test lead supported by the substrate, the second test lead including:
a first area extending into the sample chamber;
a second area extending from the sample chamber to a readout region;
a reference cell;
a reference lead, including:
a first area in electrical contact with the reference cell;
a second area extending from the reference cell to a readout region;
a filter, wherein at least a portion of the filter overlaps at least a portion of each of the first area of the first test lead, the first area of the second test lead, and the first area of the reference lead; and
a gel volume, wherein the gel volume includes a first layer in contact with the reference cell and a second layer over the first layer, wherein the first layer differs in composition from the second layer, wherein the first layer comprises about a water based gel containing about 4% agarose and about 1% hydroxyethyl cellulose, and wherein the second layer comprises a water based gel containing about 4% agarose and about a 3M concentration of KCl.

11. The device of claim 10, wherein at least a portion of the first test lead, the reference cell, at least a portion of the reference lead, and a bridge are between the substrate and the overlay when the overlay is interconnected to the substrate, wherein the overlay includes an aperture, wherein the aperture corresponds to at least a portion of the sample chamber when the overlay is interconnected to the substrate, wherein the filter is at least partially contained within the sample chamber, and wherein the gel volume is in communication with the sample chamber.

12. The device of claim 10, wherein the reference cell includes a silver/silver chloride reference cell.

13. The device of claim 10, further comprising:
a fluid sample, wherein the fluid sample comprises a wetting agent that wets the filter that electrically interconnects the first area of the first test lead, the first area of the second test lead, and the first area of the reference lead.

14. The device of claim 13, wherein the fluid sample is whole blood.

15. The device of claim 10, wherein the first test lead, the second test lead, and the reference lead are formed from an electrically conductive material having a constant composition.

16. The device of claim 15, wherein the electrically conductive material having a constant composition is platinum.

17. The device of claim 10, wherein the first test lead, the second test lead, and the reference lead are accessible to a test device in the readout region when the overlay is interconnected to the substrate.

18. The device of claim 10, wherein the first test lead, the second test lead, and the reference lead are located on a common plane.

19. An oxidation-reduction potential test device, comprising:
a substrate;
a spacer layer interconnected to at least a portion of the substrate, wherein the spacer layer defines a sample chamber;
a test strip overlay, wherein the test strip overlay is interconnected to at least a portion of the spacer layer;
a first test lead supported by the substrate, the first test lead including:
a first area extending into the sample chamber;
a second area extending from the sample chamber to a readout region;
a second test lead supported by the substrate, the second test lead including:
a first area extending into the sample chamber;
a second area extending from the sample chamber to a readout region;
a reference cell;
a reference lead, including:
a first area in electrical contact with the reference cell;
a second area extending from the reference cell to a readout region;
a filter, wherein at least a portion of the filter overlaps at least a portion of each of the first area of the first test lead, the first area of the second test lead, and the first area of the reference lead; and
a gel volume, wherein the gel volume includes a first layer in contact with the reference cell and a second layer over the first layer, wherein the first layer differs in composition from the second layer, wherein the first layer is an isolation layer, and wherein the second layer is an electrolyte layer.

20. The device of claim 19, wherein the isolation layer is a molecular screening layer.

21. The device of claim 19, wherein the electrolyte layer is a source of chloride ions.

22. The device of claim 19, wherein at least a portion of the first test lead, the reference cell, at least a portion of the reference lead, and a bridge are between the substrate and the overlay when the overlay is interconnected to the substrate, wherein the overlay includes an aperture, wherein the aperture corresponds to at least a portion of the sample chamber when the overlay is interconnected to the substrate, wherein the filter is at least partially contained within the sample chamber, and wherein the gel volume is in communication with the sample chamber.

23. The device of claim 19, wherein the reference cell includes a silver/silver chloride reference cell.

24. The device of claim 19, further comprising:
a fluid sample, wherein the fluid sample comprises a wetting agent that wets the filter that electrically interconnects the first area of the first test lead, the first area of the second test lead, and the first area of the reference lead.

25. The device of claim 24, wherein the fluid sample is whole blood.

26. The device of claim 19, wherein the first test lead, the second test lead, and the reference lead are formed from an electrically conductive material having a constant composition.

27. The device of claim 26, wherein the electrically conductive material having a constant composition is platinum.

28. The device of claim 19, wherein the first test lead, the second test lead, and the reference lead are accessible to a test device in the readout region when the overlay is interconnected to the substrate.

29. The device of claim 19, wherein the first test lead, the second test lead, and the reference lead are located on a common plane.

* * * * *